US012758157B2

(12) United States Patent
McGrath et al.

(10) Patent No.: US 12,758,157 B2
(45) Date of Patent: Oct. 13, 2026

(54) PUPILLARY CURVE MORPHOLOGY AND DIAGNOSIS MANAGEMENT

(71) Applicant: Apertur Inc., Seattle, WA (US)

(72) Inventors: Lynn B. McGrath, New York, NY (US); Anthony Maxin, Seattle, WA (US); Robin Alfieri, Seattle, WA (US)

(73) Assignee: Apertur Inc., Seattle, WA (US)

( * ) Notice: Subject to any disclaimer, the term of this patent is extended or adjusted under 35 U.S.C. 154(b) by 364 days.

(21) Appl. No.: 18/516,392

(22) Filed: Nov. 21, 2023

(65) Prior Publication Data

US 2025/0160760 A1 May 22, 2025

(51) Int. Cl.
*A61B 5/00* (2006.01)
*A61B 5/16* (2006.01)

(52) U.S. Cl.
CPC ............ *A61B 5/7267* (2013.01); *A61B 5/163* (2017.08); *A61B 5/7275* (2013.01); *A61B 2560/0223* (2013.01); *A61B 2560/0242* (2013.01)

(58) Field of Classification Search
CPC ..... A61B 5/7267; A61B 5/163; A61B 5/7275; A61B 2560/0223; A61B 2560/0242
See application file for complete search history.

(56) References Cited

U.S. PATENT DOCUMENTS

| | | | | |
|---|---|---|---|---|
| 6,539,100 | B1 | 3/2003 | Amir et al. | |
| 11,538,351 | B1 | 12/2022 | Bruni et al. | |
| 2016/0026847 | A1 | 1/2016 | Vugdelija et al. | |
| 2019/0130297 | A1 | 5/2019 | Linden | |
| 2019/0191995 | A1* | 6/2019 | Giovinazzo ............ | A61B 3/113 |
| 2020/0110341 | A1 | 4/2020 | Mossavat et al. | |
| 2020/0348755 | A1 | 11/2020 | Gebauer et al. | |
| 2023/0052100 | A1* | 2/2023 | Devani .................. | A61B 3/112 |
| 2023/0360220 | A1* | 11/2023 | Rotenstreich ........ | A61B 5/0261 |

FOREIGN PATENT DOCUMENTS

WO WO2023021509 A1 2/2023

OTHER PUBLICATIONS

Medathati, Naga Venkata Kartheek, Ruta Desai, and James Hillis. "Towards inferring cognitive state changes from pupil size variations in real world conditions." ACM Symposium on Eye Tracking Research and Applications. 2020. (Year: 2020).*

(Continued)

*Primary Examiner* — Amanda L Steinberg
(74) *Attorney, Agent, or Firm* — Lee & Hayes, P.C.

(57) ABSTRACT

Techniques for calculating or managing pupillary curve data identified based on data associated with computing devices are discussed herein. For example, a machine learning (ML) model can be utilized to analyze sensor data collected by a camera associated with a computing device. The ML model can perform a comparison between a pupillary (e.g., a pupil response curve and previous pupillary curves (e.g., previous pupil response curves) utilizing classification information associated with the previous pupil response curves. The comparison can be utilized to identify a physiological condition associated with the pupil response curve. Information identifying the physiological condition can be presented by a display or transmitted to the computing device.

20 Claims, 5 Drawing Sheets

(56) References Cited

OTHER PUBLICATIONS

Ajasse, et al., "Computerized Biofeedback to characterize Pupil Cycle Time (PCT) in neuropathies and retinopathies"retrieved on Jan. 8, 2025 at <<http://www.medrxiv.org/content/medrxiv/early/2022/05/26/2022.05.24.22275446.full.pdf>>, medRxiv, May 24, 2022, pp. 1-17.

Jin, et al., "Pupil and Blink Detection algorithms for wearable eye tracking system", retrieved on Jan. 8, 2025 at <<https://assets-eu.reseachsquare.com/files/rs-1592196/vl/50a42ae0-flfa-422c-8490-63f5534a6f0f.pdf?c=1666602876>>, Research Square, May 4, 2022, pp. 1-21.

Kaczorowska, et al., "Intepretable Machine Learning Models for three-way classification of cognitive workload levels for eye-tracking features", retrieved on Jan. 8, 2025 at <<https://pmc.ncbi.nlm.nih.gov/articles/PMC7914927>>, Brain Sciences, vol. 11.2, Feb. 9, 2021, pp. 1-22.

Pinheiro, et al., "Pupillary Light Reflex as a diagnostic aid from computational viewpoint: A systematic literature review", retrieved on Jan. 8, 2025 at <<http://www.sciencedirect.com/science/article/pii/S1532046421000861>>, Journal of Biomedical Informatics, vol. 117, No. 103757, Dec. 26, 2020, pp. 1-17.

Search Report and Written Opinion for International Application No. PCT/US2024/056838, Dated Jan. 21, 2025, 14 pages.

Xin, et al., "Detecting Task Difficulty of Learners in Colonoscopy Evidence from Eye Tracking", retrieved on Jan. 8, 2025 at <<https://pmc.ncbi.nlm.nih.gov/articles/PMC8327395>>, Journal of Eye Movement Research, vol. 14.2, Jul. 13, 2021.

* cited by examiner

PUPILLARY CURVE MORPHOLOGY AND DIAGNOSIS MANAGEMENT

BACKGROUND

Medical devices measure characteristics associated with pupils to identify various types of pupillary metrics. The metrics are utilized as status and/or health indicators of the pupils and thereby, of the patient. The medical devices include pupillometers, such as automated pupillometers and handheld pupillometers. The pupillometers have light sources that emit light at pupils, and sensors that detect reflected light representing aspects of pupils. Data is captured by the pupillometers and utilized to identify the aspects of the pupils, which include pupillary light reflexes (PLRs), pupil diameters, and pupil sizes. The pupillary metrics are identified for the PLRs, the pupil diameters, and the pupil sizes and utilized to diagnose medical conditions. The medical conditions include pathological medical conditions, such as neurodegenerative disorders, mental health disorders, and diseases. Other medical devices utilized to measure other aspects of the pupils include pupillary distance (PD) meters and pupillary reflex devices. The PD meters, which include optical digital PD meters, are utilized to measure are interpupillary distances (IPDs) (or "binocular PDs"), which are distances between centers of two pupils. The pupillary reflex devices, such as penlights, illuminate pupils and enable subjective measurements of the PLRs during pupil examinations.

DETAILED DESCRIPTION

Figure 1:
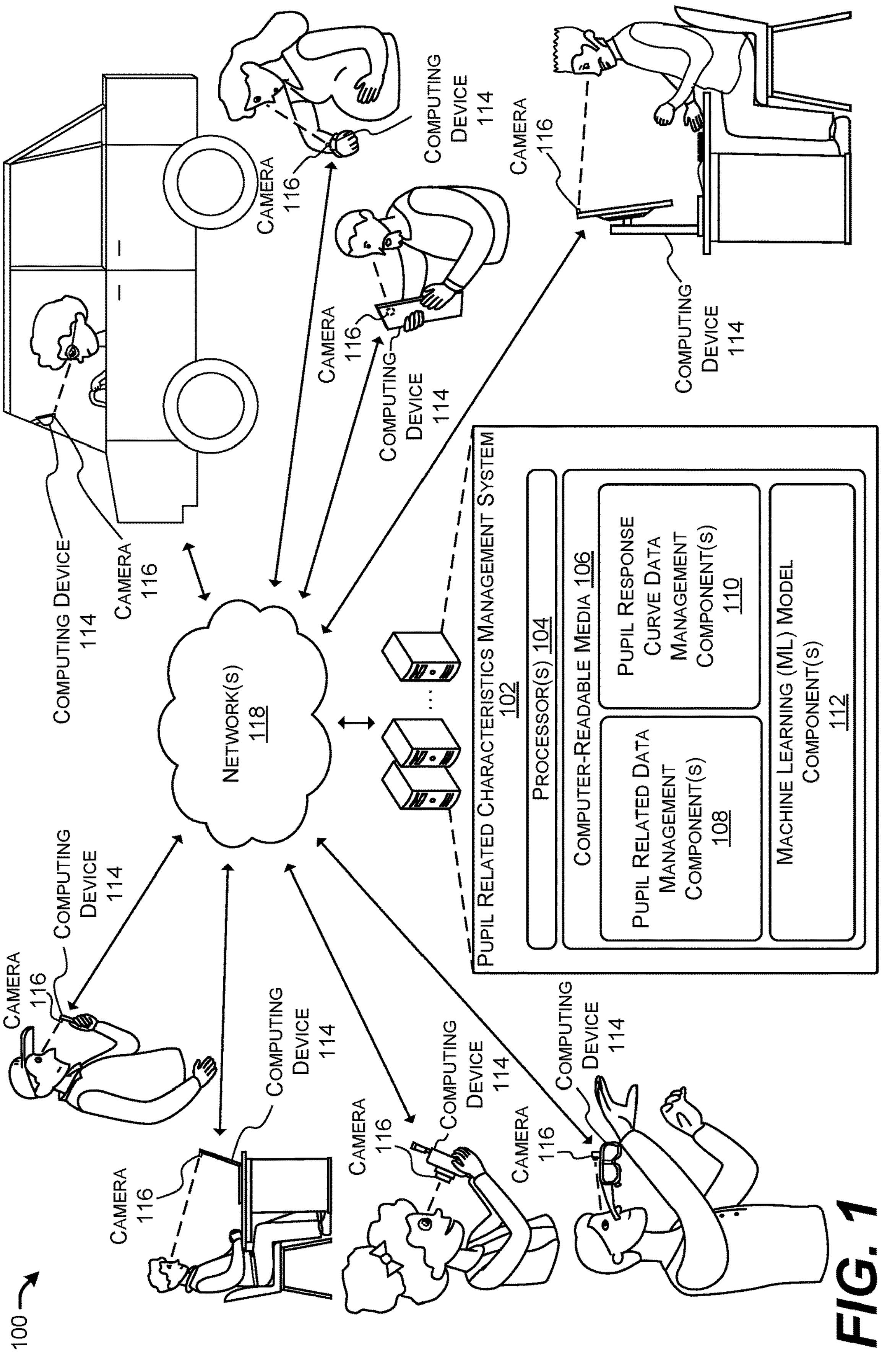
FIG. 1 depicts an example environment with devices, systems, and networks for performing pupillary curve morphology and diagnosis management.

Techniques for managing pupillary curve data identified based on data associated with computing devices are discussed herein. For example, pupil related characteristics management systems can be utilized to manage pupillary activity databases and pupil related characteristics databases. The pupillary activity databases can store pupillary activity data. The pupil related characteristics databases can store pupil related characteristics information. The pupil related characteristics management systems can identify the pupillary data, which can include the pupillary activity data and which can be utilized to identify pupil related characteristics information. The pupil related characteristics information can include pupil response curve related information. The pupil related characteristics information can be identified utilizing machine learning (ML) models, which can be trained utilizing training pupillary data and training pupil related characteristics information.

The pupillary data can be identified based on sensor data captured by sensors (e.g., visible light sensors, infrared sensors, ultrasonic sensors, etc., or any combination thereof) of the computing devices. The sensor data can be associated with pupillary activity of users associated with the computing devices. The sensor data can be utilized to identify datasets including portions of the pupillary data. The datasets being identified by the ML models can be utilized to identify physiological conditions associated with current sensor data. The physiological conditions can be identified by performing comparisons between current datasets and the datasets stored in the pupillary databases. The current datasets can be associated with current pupillary data identified utilizing the current sensor data.

The pupil related characteristics information can be stored in the pupil related characteristics databases, which can be utilized by the pupil related characteristics management systems to manage various types of the pupil related characteristics information in various ways. The pupil related characteristics information can include groups of pupillary characteristics. The pupil related characteristics information can be identified based on pupil response data. The pupil response data can include pupillary activity curves, which can include pupil response curves. Individual ones of the groups of the pupillary characteristics can be identified based on corresponding pupil response curves in the pupil response curve data.

The pupil related characteristics databases can include pupil related characteristics library databases, which can include pupil response curve library databases. Individual ones of the datasets can store corresponding datasets utilized to identify corresponding pupil response curves in corresponding portions of the pupil response curve data. The pupil related characteristics information can include classification tag information, which can include classification tags associated with classifications identified based on the pupil response curve data. The pupil related characteristics information, including the pupil response curve data and the classification tag information, can be stored in the pupil related characteristics databases.

The ML models, which can be trained based on the training pupillary data and the training pupil related characteristics information, can utilize pupillary data to identify pupil related characteristics information. The pupil related characteristics management systems, which can be utilized to manage the ML models, can input the pupillary data to the ML models. The pupil related characteristics management systems can identify the pupil related characteristics information being output by the ML models based on analysis of the pupillary data.

The pupillary data can be analyzed utilizing mathematical algorithms to perform comparisons between the training pupil related characteristics information and current pupil related characteristics information based on baselines and classifications. The baselines can include various pupil response curves, which can be identified as being associated with various corresponding types of classifications based on the training pupillary data and the training pupil related characteristics information. The classifications, which can include mathematically generated classifications, can be identified via classification tags included in the pupil related characteristics information. Individual ones of pupil response curves, which can be identified based on the corresponding datasets of the pupillary data, can be utilized to identify the pupil related characteristics information, along with corresponding classification tags, by the ML models.

The pupil related characteristics management systems can input pupillary data received from the computing devices, utilize the ML models to analyze the pupillary data, and perform various types of actions based on output of the ML models. The pupillary data can be identified based on sensor data received from collections of the computing devices. Individual ones of the datasets of the pupillary data can be identified based on corresponding groups of sensor data captured by corresponding computing devices in the collections of the computing devices.

The datasets of the pupillary data can be analyzed by operation of the ML models to output the pupil related characteristics information and physiological condition identifiers. Individual ones of the physiological condition identifiers, which can be associated with corresponding pupil response curves in corresponding groups of the pupil related characteristics information, can be identified and output. The pupil related characteristics management systems can transmit individual groups of physiological condition information associated with corresponding physiological conditions, with which the physiological condition identifiers are associated, to corresponding computing devices.

The pupil related characteristics management systems can cause presentation of individual groups of the physiological condition information, along with corresponding groups of the pupil related characteristics information, by corresponding computing devices. The pupil related characteristics management systems can perform various other types of management related actions, cause performance by the computing devices of various other types of computing device related actions, or any combination thereof, based on the pupil related characteristics information and/or the physiological condition information.

Utilizing the pupil related characteristics management systems has many technical benefits. For example, compute resources utilized by the pupil related characteristics management systems to identify pupil response curves according to the techniques discussed herein are relatively fewer than for existing systems that do not possess pupil response curve generation capabilities. Because existing pupil related sensor data processing systems operating according to conventional techniques utilize data from current pupillometers, physiological conditions are not efficiently and correctly identified. As a result, larger occurrences of processing of sensor data captured by the pupillometers are required to be redundantly performed over extended periods of time by existing sensor data processing systems. Large numbers of disparate and disconnected existing systems, some of which are utilized to manage data captured by pupillometers and others which are utilized to manage data captured by image sensors, often never produce data suitable for effective identifications of physiological conditions. In contrast to the existing systems that includes combinations of incompatible systems utilized to perform relatively large amounts of redundant, and/or unnecessary, data processing, the pupil related characteristics management systems according to the techniques discussed herein consistently, reliably, and efficiently process and analyze sensor data to accurately identify the pupil response curves and the physiological conditions.

Moreover, compute resources utilized to perform data analysis by the pupil related characteristics management systems according to the techniques discussed herein are relatively fewer in contrast to existing systems. The pupil related characteristics management systems efficiently process sensor data captured by various computing devices to analyze the sensor data and identify PLRs. Sensor data being captured by computing devices operating according to conventional techniques is not analyzed for capturing any PLRs. By utilizing the techniques discussed herein, the pupil related characteristics management systems manage the sensor data captured by the computing devices for identifying PLRs, as well as enabling communications utilizing the computing devices, in contrast to existing devices that are required to perform redundant analysis utilizing specialized pupillometers to identify PLRs, in addition to communications being managed for computing devices.

Compute resources of the computing devices that transmit the sensor data to the pupil related characteristics management systems according to the techniques discussed herein are also conserved. Unlike pupillometers that capture sensor data resulting in uncertain and unusable analysis results according to conventional techniques, the computing devices operating according to the techniques discussed herein provide sensor data that is utilized by the pupil related characteristics management systems to generate pupil response curves. The pupil response curves being utilized to produce results identifying physiological conditions accurately based on the sensor data provided by the computing devices enable portions of the compute resources of the computing devices that are not being redundantly expended otherwise to be reallocated to enable processing of other tasks.

Network resources utilized for transmission of data between the pupil related characteristics management systems and the computing devices according to the techniques discussed herein are also conserved. Large numbers of data captures are required to be performed by pupillometers, and to be analyzed by data management systems, according to the techniques discussed herein. However, current data management systems that do not generate pupil response curves are unable to accurately obtain identifications of physiological conditions for patients, resulting in redundant transmissions of data that is ineffectively utilized over large periods of time. In contrast to existing systems that require ongoing communications of data without reliable generation of analysis results, the networks communication of the pupil response curves according to the techniques discussed herein efficiently and accurately utilize communicated data to identify physiological conditions. Network resources that would otherwise be expended by systems utilizing conventional techniques are able to be reallocated for other purposes by utilizing the pupil related characteristics management systems and the computing devices that operate according to the techniques discussed herein.

Memory resources utilized by the pupil related characteristics management systems and the computing devices according to the techniques discussed herein are also conserved. According to existing technology, current data management systems store pupillometry data, which is unable to be efficiently and effectively utilized for correct identification of physiological conditions. As a result, the data is unnecessarily stored, in such systems. Often large numbers of existing systems store redundant data due to the data being captured by different pupillometers, due to the systems not being networked together, and due to the systems not being able to be collectively utilized to generate effective results that correctly identify physiological characteristics. In contrast to existing systems, the pupil related characteristics management systems according to the techniques discussed herein collaboratively manage sensor data received from the computing devices, to generate pupil response curves and physiological condition identifications, which results in vastly more efficient utilization of memory resources of the pupil related characteristics management systems as well as the computing devices.

FIG. 1 depicts an example environment 100 with devices, systems, and networks for performing pupillary curve morphology and diagnosis management. The environment 100 can include a pupil related characteristics management system 102. The pupil related characteristics management system 102 can include one or more processors and one or more computer-readable media 106. The computer-readable media 106 can be utilized to store one or more data management components (e.g., one or more pupil related data management components 108), one or more pupil related characteristics information management components (e.g., one or more pupil response curve data management components 110), one or more machine learning (ML) model components 112, or any combination thereof.

The pupil related characteristics management system 102 can be communicatively coupled to one or more computing devices 114, one or more camera devices (or "camera(s)") 116, or any combination thereof. The pupil related characteristics management system 102 can be communicatively coupled to the computing device(s) 114 and/or the camera(s) 116 via one or more networks 118.

The computing device(s) 114 may represent, but are not limited to, televisions (TVs), cellular telephones, desktop computers, server computers or blade servers such as web-servers, map-reduce servers, or other computation engines or network-attached storage units, personal computers, mobile computers, laptop computers, tablet computers, telecommunication devices (e.g., mobile phones, cellular phones, etc., or any combination thereof), wearable devices (e.g., digital watches, glasses (e.g., augmented reality (AR) glasses, virtual reality (VR) glasses, or any combination thereof, etc.)), optical devices (e.g., ophthalmological devices, optometrist devices, pupil related devices, pupillometers, or any combination thereof), network enabled televisions, thin clients, terminals, personal data assistants (PDAs), game consoles, gaming devices, work stations, media players, personal video recorders (PVRs), set-top boxes, cameras, integrated components for inclusion in a computing device, appliances, vehicle computers (e.g., rear-view mirror computers), building security devices (e.g., home security devices (e.g., front door security devices)), field devices, handheld devices, internet of things (IoT) devices, robotic devices, voice-enabled device(s), or any other sort of computing device coverable of sending communications and performing the functions according to the techniques described herein. Among these TVs are liquid crystal display (LCD) TVs, light emitting diode (LED) TVs, organic light emitting diode (OLED) TVs, plasma display devices (PDP) TVs, quantum dot (QLED) TVs, and electroluminescent (ELD) TVs. In some examples, the voice-enabled device(s) of the computing device(s) 114 may include devices with or without display components. In some examples, the display device(s) of the computing device(s) 114 may include devices with or without speech processing components.

In various examples, individual ones of the computing device(s) 114 and/or individual ones of the camera(s) 116 can include one or more sensors. For instance, individual ones of the computing device(s) 114 and/or individual ones of the camera(s) 116 can include one or more infrared sensors, one or more ultrasonic sensors, one or more position sensors, one or more photoelectric sensors, one or more motion sensors, one or more pressure sensors, one or more proximity sensors, one or more accelerometers, one or more light detection and ranging (lidar) sensors, one or more other sensors of other types, or any combination thereof.

In some examples, the network(s) 118 can include one or more of various type of networks (e.g., the Internet, wireless wide area networks (WANs), personal area networks (PANs), wired and/or wireless local area networks (LANs), etc.). The network(s) 118 can include any type of network or combination of networks, including wired and/or wireless networks. In some embodiments, the computing device(s) 114 and/or the camera(s) 116 can include one or more transceivers (e.g., one or more wireless transceivers of any type), one or more connectors (e.g., one or more connectors for wire communications of any type), or any combination thereof.

In some embodiments, the computing device(s) 114 can access one or more network-based services of the pupil related characteristics management system 102, such as, without limitation, via an application (e.g., a computing device application) (e.g., a mobile device application), a web-based console, a software-development kit (SDK), a command-line interface (CLI), an application programming interface (API), and/or any other suitable means.

Although the pupil related data management component(s) 108, the pupil response curve data management component(s) 110, and/or the ML model component(s) 112 can be separate from one another, as discussed above in the current disclosure, it is not limited as such. In some examples, at least one of any of the pupil related data management component(s) 108, the pupil response curve data management component(s) 110, and/or the ML model component(s) 112 can be combined with one another, implemented as a single component or a combination of components, and/or integrated together in any way.

Although individual ones of the computing device(s) 114 and the corresponding camera(s) 116 can be separate from one another, as discussed above in the current disclosure, it is not limited as such. In some examples, any number of individual ones of the computing device(s) 114 and the corresponding camera(s) 116 may be combined with one another, may be implemented as a single component or a combination of components, and/or may be integrated together in any way.

The pupil related characteristics management system 102 can receive data (or "received data"), which can include data (or "computing device data") received from the computing device(s) 114 and/or data (or "camera data") received from the camera(s) 116. In some examples, the data (e.g., the received data) being received may be based on data (or "sensor data") (e.g., generated data) (or "captured data") associated with (e.g., being generated by) (e.g., being captured by) the camera(s) 116. In those or other examples, the received data can include a portion (e.g., a partial portion or an entire portion) of the sensor data, which can be transmitted (e.g., transmitted by individual ones of the computing device(s) 114, individual ones of the camera(s) 116, or any combination thereof), as transmitted data, to the pupil related characteristics management system 102.

Although the terms "sensor data," "captured data," "generated data," "transmitted data," "received data," etc., are utilized for simplicity and ease of explanation throughout the current disclosure, as discussed herein, it is not limited as such. In various examples, any of the terms "sensor data," "captured data," "generated data," "transmitted data," "received data," etc. may be interpreted as being interchangeably utilized to refer to any portion (e.g., a partial portion or an entire portion) of data being captured and/or transmitted by the computing device(s) 114, the camera(s)

116, etc., and/or being received by the pupil related characteristics management system 102, for purposes of implementing any of the techniques discussed herein.

In some examples, the captured data may be based on light (e.g., one or more light beams, any of which may include a bundle of at least one ray of light) (e.g., one or more rays of light). For instance, the captured data may be based on the light being emitted, as emitted light (or "transmitted light"), the light (e.g., the emitted light) that is emitted being reflected, as reflected light, and/or the light (e.g., the reflected light) that is reflected being received, as received light.

In various implementations, the data (e.g., the captured data) being captured by the camera(s) 116 can include sensor data, which can include image data (e.g., one or more images), video data (e.g., one or more videos), or any combination thereof. In those or other examples, at least one portion of the data being received from the computing devices(s) 114 and/or the camera(s) 116 can be received dynamically (e.g., live, or in real time) during generation (e.g., capturing) of the sensor data. In those or other examples, at least one portion of the data being received from the computing devices(s) 114 and/or the camera(s) 116 can be received during playback (e.g., playback by the computing device(s) 114) of the data. In those or other examples, at least one portion of the data being received from the computing devices(s) 114 and/or the camera(s) 116 can be received at any time based on the data being stored in the computing devices(s) 114.

In some examples, at least one portion of the data being received from the computing devices(s) 114 and/or the camera(s) 116 can be received at any time based on there being no concurrent (e.g., no simultaneous or contemporaneous) generation and/or playback of the data. For instance, with examples in which there is no concurrent (e.g., no simultaneous or contemporaneous) generation and/or playback of the data, the at least one portion of the data being received from the computing devices(s) 114 and/or the camera(s) 116 can be received at any time based on completion of a portion (e.g., a partial portion or an entire portion) of generation of the data and/or completion of a portion (e.g., a partial portion or an entire portion) of playback of the data.

In various implementations, the pupil related characteristics management system 102 can identify pupillary data based on the reflected data (e.g., the sensor data), via a scan (e.g., a simultaneous scan of at least one pupil). The sensor data can be associated with pupillary activity of users associated with the computing device(s) 114. The sensor data can be utilized to identify one or more datasets including one or more corresponding portions of the pupillary data.

The pupil related characteristics management system 102 can utilize the pupil related data management component(s) 108 to identify the dataset(s). The pupil related data management component(s) 108 can analyze the sensor data and identify, based on the sensor data, the pupillary data (e.g., the dataset(s) including the corresponding portion(s) of the pupillary data).

In various implementations, the pupillary data can include data associated with one or more pupils of the user. For example, the pupillary data, which can include data associated with individual ones of one or more pupils of the user, can include corresponding diameters of one or more diameters, corresponding sizes of one or more sizes, corresponding PLRs of one or more PLRs, any other pupillary data of various types, or any combination thereof.

In some examples, a "binocular concept" can be utilized for collection of the sensor data. The "binocular concept," which can be utilized to collect data for both eyes at the same time, can be utilized to identify how both pupils react to one or more light stimuli (e.g., one or more light rays and/or light beams directed at individual ones of the eyes), one or more non-light stimuli (e.g., one or more colors being presented in a view (e.g., a line of sight of the eyes) on one or more media of any type, such as one or more sheets of paper (e.g., one or more printed advertisements)), one or more of any other types of stimuli, or any combination thereof. In contrast to conventional technology that is limited to a "monocular concept" in which data is collected individually for a single eye, the "binocular concept" as discussed throughout the current disclosure beneficially provides more accurate and comprehensive sensor data. By increasing the accuracy of the sensor data, the accuracy of pupillary data being identified according to the techniques discussed herein is increased.

As a hypothetical example, such as for instances in which non-light stimuli is utilized, alternatively or additionally to light stimuli, to capture the sensor data and/or to identify the pupil response curve(s), as discussed below in further detail, a non-stimuli approach can be utilized without light stimuli (e.g., without any particular/designated light stimuli). In various examples, by capturing the sensor data and/or identifying the pupil response curve(s) without requiring measurement/computing/medical device drive light stimuli, such as by, instead, using one or more images (e.g., one or more photos, one or more visual stimuli of any type, etc.), one or more videos, and/or one or more audible stimuli (e.g., one or more verbal utterances, etc., spoken) output to the user (e.g., a patient undergoing examination), one or more responses (e.g., one or more pupil responses) of any type may be identified. For instance, in drug/alcohol rehab, the image(s) (e.g., the photos) can be presented in a line of sight of a patient and utilized to detect one or more metrics, and/or, based on the metric(s), a probability of one or more chances of a relapse by the patient.

The pupillary data can include data associated with one pupil or both pupils of the user. For instance, with examples in which the pupillary data includes data associated with both pupils of the user, the pupillary data can be based on sensor data collected simultaneously and/or contemporaneously for both pupils. In some examples, a portion of time, which can include an interval and/or a time period, and which can be utilized to collect data for a pupil, can overlap with another portion of time (e.g., another portion of time, which can include another interval and/or another time period, respectively and which can be utilized to collect data for another pupil).

In those or other examples, a start time and/or an end time utilized to collect the sensor data for a pupil can be different from another start time and/or another end time, respectively, utilized to collect the sensor data for another pupil. In those or other examples, individual ones of one or more differences between a start time and/or an end time utilized to collect the sensor data for a pupil in comparison to another start time and/or another end time, respectively, utilized to collect the sensor data for another pupil, can be less than corresponding thresholds. For instance, an amount of an overlap of time between a portion of time utilized to collect data for a pupil, and another portion of time utilized to collect data for another pupil can be greater than a threshold overlap (e.g., the overlap can be sufficient to enable complete collection of the sensor data for both pupils).

Although the sensor data can be collected for both pupils simultaneously and/or contemporaneously as discussed above in the current disclosure, it is not limited as such. In some examples, a portion of time, which can include an interval and/or a time period, and which can be utilized to collect data for a pupil, can be different from another portion of time (e.g., another portion of time, which can include another interval and/or another time period, respectively and which can be utilized to collect data for another pupil). In those or other examples, a start time and an end time utilized to collect the sensor data for a pupil can be different from another start time and another end time, respectively, utilized to collect the sensor data for another pupil.

In alternative examples, sensor data obtained for a user can include single-eye sensor data. For instance, sensor data can be collected for a single eye, without any sensor data being collected for another eye.

In some examples, the pupil related characteristics management system 102 can identify pupillary activity curve data. For example, the pupil related characteristics management system 102 can utilize the pupil response curve data management component(s) 110 to identify the pupillary activity curve data. In some cases, the pupillary activity curve data can include one or more pupillary activity curves.

Although the pupil response curve data management component(s) 110 can be utilized to identify the pupillary activity curve data as discussed above in the current disclosure, it is not limited as such. In some examples, the pupil response curve data management component(s) 110 can include one or more of various types of pupil response curve data management components, including one or more pupillary light reflex (PLR) curve data management components, one or more other types of curve data management component(s), or any combination thereof, the various type(s) of the pupil response curve data management component(s) being utilized in a similar way as for the pupil response curve data management component(s) 110 for purposes of implementing any of the techniques as discussed herein.

In various cases, the pupillary activity curve data can include pupil response curve data, which can include one or more pupil response curves. For example, individual ones of the pupillary activity curve(s) being identified by the pupil related characteristics management system 102 can include corresponding pupil response curves. In some cases, the pupil related characteristics management system 102 can utilize the identified pupil response curve data management component(s) 110 to identify the pupillary activity curve(s) (e.g., the pupil response curve(s)).

Although the pupillary activity curve data can include pupil response curve data, which can include the pupil response curve(s), as discussed above in the current disclosure, it is not limited as such. In some examples, the pupillary activity curve data can include one or more of various types of curve data, including one or more PLR curve data, one or more other types of curve data, or any combination thereof; and the pupillary activity curve(s) can include one or more of various types of curves, including one or more PLR curves, one or more other types of curves, or any combination thereof, the various type(s) of the curve data and/or the various type(s) of the curve(s) being utilized in a similar way as for the pupil response curve data and/or the pupil response curve(s), respectively, for purposes of implementing any of the techniques as discussed herein.

In various implementations, the pupil response curve data can be identified based on the sensor data and/or the pupillary data. In some examples, the pupil related characteristics management system 102 can utilize the pupil response curve data management component(s) 110 to analyze the sensor data and/or the pupillary data, and to identify the pupil response curve data based on the sensor data and/or the pupillary data. Individual ones of the pupil response curve(s) can be identified based on corresponding diameters, corresponding sizes, corresponding PLRs, any other corresponding pupillary data, or any combination thereof.

In various examples, the sensor data can be identified as the pupillary data, which can be utilized to identify the pupil response curve data. For instance, with examples, in which the pupillary data is utilized to identify the pupil response curve data, the pupillary data can include data (e.g., raw sensor data (or "raw data")) that is smoothed, cleaned, polished, filtered, refined, etc., or any combination thereof, or modified utilizing one or more other operations of various types (e.g., a smoothing operation, a cleaning operation, a polishing operation, a filtering operation, a refining operation, and/or one or more other operations of other types).

In some instances, processing the raw sensor data includes processing the raw sensor data via a path beginning with the raw sensor data (e.g., captured video data) and including generation of a pupil response curve based on the raw sensor data. For example, the raw sensor data is processed and utilized to extract the pupil response curve from the raw sensor data. The raw sensor data is input to a computer vision algorithm that detects one or more pupil boundaries (e.g., individual pupil boundaries associated with corresponding pupils). For each frame of a video (e.g., a video associated with the captured video data) and before any smoothing and/or filtering steps of the video, the computer vision algorithm calculates a diameter of individual ones of the pupils and generates the pupil response curve utilizing the calculated diameters (e.g., individual ones of the diameters are identified as corresponding points of the pupil response curve).

In some examples, the pupil related characteristics management system 102 can utilize the ML model component(s) 112 to identify (e.g., determine, analyze, modify, etc., or any combination thereof) the data (e.g., the pupillary data) in the pupil related data management component(s) 108 and to identify the (e.g., determine, generate, capture, modify, etc., or any combination thereof) the information (e.g., the pupil response curve data) in the pupil response curve data management component(s) 110. In various cases, the pupillary data can be analyzed by one or more ML models to identify the pupillary activity curve data (e.g., the pupil response curve data). In various cases, individual ones of the ML model component(s) 112 can include a corresponding plurality of at least one of the ML model(s).

In some cases, individual ones of the ML model(s) can be identified by the pupil related characteristics management system 102 as being applicable for analysis. In various implementations, one or more "meta models" can be utilized by the pupil related characteristics management system 102 for identifying "appropriate" ML model(s) for any analysis that is performed. For example, based on the pupil response curve data, the meta ML model can identify which of the ML model(s) is likely to generate efficient and accurate data, with respect to other ML model(s).

The ML model(s) being likely to generate efficient and accurate data can be identified based on a likelihood being identified as being greater than one or more other likelihoods associated with other ML model(s), and/or based on the likelihood being greater than a threshold likelihood. In some cases, the meta model can be included as an overarching coordinating algorithm allowing decisions to be made for which of the ML model(s) is to be used and in what circumstances (e.g., for which types of pupil response curve (s)).

In some implementations, pupillary activity curves (e.g., pupil response curves) can be generated and submitted to analysis via mathematical algorithms to preserve any and all data that is "cooked" into the curves. In contrast to existing systems that perform operations including taking measurements with pupil response devices (e.g., pupillometers), which results in significant limitations regarding efficacy and usefulness of the operations, pupil response measurements and pupil response curve generations according to the techniques discussed herein greatly increase the amounts, the forms, the utilities, and the applications of the results that can be achieved by generating and analyzing the pupil response curves.

In some examples, the systems operating according to the techniques discussed herein receive, without performance of intervening analysis and/or measurements (e.g., without intermediate metric computations), all of the pupillary activity curves (e.g., pupil response curves) for analysis. Whole pupil response curves (e.g., whole "pictures" of curves) can be processed, by ML models and utilizing complex mathematical algorithms, to identify one or more patterns and/or one or more characteristics in the results which can be utilized for diagnosis of physiological conditions.

In contrast to existing systems that perform pupil response measurements, utilizing the whole pupil response curves according to the techniques discussed herein enables results to be produced that might have been missed otherwise. Generation of various types of patterns, identifiers, signature characteristics, etc., which might be utilized for the physiological condition diagnosis, is possible utilizing the analysis of the pupil response curves according to the techniques discussed herein. Wholistic inspection and analysis of the pupil response curves utilizing various mathematical computations greatly increases accuracy and effectiveness of the physiological condition diagnosis.

For example, subtle indicators that might otherwise have been missed utilizing conventional techniques can be identified and utilized for more thorough and complete physiological condition diagnosis according to the techniques discussed herein. In some instances, while "known unknowns" may be assumed for purposes of performing pupillary data measurements, the techniques discussed herein also enable "unknown unknowns" to be identified, which would otherwise have been overlooked, to enable more efficient and effective methods and strategies for diagnosing physiological conditions to be identified.

The pupillary activity curve data (e.g., the pupil response curve data) can include various types of curve data, which can include pupillary activity curves (e.g., pupil response curves) associated with various types of data. In various cases, individual ones of the pupillary activity curve(s) (e.g., the pupil response curve(s)) can include one or more corresponding portions of time series curve data. For example, a pupil response curve can include time series curve data (e.g., a portion of time series curve data) (e.g., the pupil response curve including data being represented by a two-dimensional line) for a pair of pupils of a user. In such an example, the pupil response curve can include the time series curve data, which can represent one or more changes (or "pupil response curve change(s)") (or "curve change(s)") (or "pupil response curve characteristic(s)") (or "curve characteristic(s)") (e.g., of one or more corresponding diameters of a pair of pupils over time, one or more changes of one or more corresponding sizes of a pair of pupils over time, any other types of one or more other changes, or any combination thereof).

Although the term "pupil response curve" is utilized for simplicity and ease of explanation to refer to data being represented by the two-dimensional line for the pupil and/or the pair of pupils of the user, as discussed above in the current disclosure, it is not limited as such. In some examples, any of the occurrences of the term "pupil response curve" as discussed herein may be interpreted as including any type of pupil response curve of any number of dimensions and/or associated with any number of pupils. In those or other examples, any occurrences of the term "pupil response curve" may be interpreted as including individual ones of one or more pupil response curves associated with corresponding pupils and/or including corresponding lines (e.g., corresponding two-dimensional lines) (e.g., corresponding three-dimensional lines) of any type, and may be utilized in a similar way as for the pupil response curve(s) for purposes of implementing any of the techniques discussed throughout the current disclosure.

In some examples, individual ones of the pupil response curve(s) can represent information (e.g., at least one curve characteristic of the curve characteristic(s)) associated with at least one pupil. In those or other examples, the pupil response curve can represent at least one change of at least one pupil in a pair of pupils with which the sensor data is associated (e.g., at least one change of diameter of at least one pupil in the pair of pupils, at least one change of size of at least one pupil in the pair of pupils, or any combination thereof).

In some examples, individual ones of the pupil response curve(s) can represent information associated with both pupils in corresponding pairs of pupils based on the corresponding pupil response curve(s) including data associated with the corresponding pairs of pupils. In those or other examples, individual ones of the pupil response curve(s) can represent information associated with single pupils in corresponding pairs of pupils based on the corresponding pupil response curve(s) including data associated with the corresponding pairs of pupils. In those or other examples, individual ones of the pupil response curve(s) can represent information associated with corresponding single pupils based on the corresponding pupil response curve(s) including data associated with the corresponding single pupils.

The pupil related characteristics management system 102 can utilize the dataset(s) to identify physiological conditions based on the sensor data. The physiological conditions can be identified by performing one or more comparisons between the dataset(s). For instance, with examples in which the dataset(s) (e.g., the dataset(s) stored in the pupillary databases and/or one or more other databases) include one or more training datasets and one or more others (e.g., one or more current datasets), the comparison(s) can include at least one comparison between at least one of the training dataset(s) and at least one of the current dataset(s). The current dataset(s) can be associated with one or more portions of current pupillary data identified utilizing one or more portions of current sensor data (e.g., sensor data being currently, simultaneously, contemporaneously, etc.) generated (e.g., dynamically generated, generated in pseudo real-time, generated in real-time, or any combination thereof).

In some examples, the light (e.g., the light beam(s)) (e.g., the ray(s) of light) (or "emitted light") being emitted can include a portion (e.g., a partial portion or an entire portion) of the light (e.g., at least one of the light beam(s) and/or at least one of the light ray(s)) being emitted by one or more sources. For example, the source(s) can include at least one of the computing device(s) 114, at least one of one or more other devices, or a combination thereof.

In various implementations, the pupil related characteristics management system 102 can manage light related data. For example, the light related data can include light type data (e.g., data associated with, and/or identifying, at least one of the type(s) of light, as discussed below in further detail), light characteristics data (e.g., data associated with, and/or identifying, at least one of characteristic(s), as discussed below in further detail), light level data (e.g., data associated with individual ones of the level(s) associated with, and/or identifying, corresponding characteristics, as discussed below in further detail), light wavelength data (e.g., data associated with, and/or identifying, at least one of the wavelength(s), as discussed below in further detail), light category data (e.g., data associated with, and/or identifying, individual ones of the category(ies), as discussed below in further detail), any other data related to the emitted light, the reflected light, the received light, any other light, any other data of various types, or any combination thereof.

In some examples, the other data being managed by the pupil related characteristics management system 102 can include device related data (e.g., data associated with, and/or identifying, at least one corresponding device of the device (s) 114) (e.g., data associated with, and/or identifying, one or more of serial numbers, details, names, light source versions and/or types, camera versions and/or types, calibration dates, calibration types, manufacturing dates, ship dates, creation dates, release dates, version dates, expiration dates, power levels, etc., or any combination thereof). In those examples, the device related data can be associated with one or more components, one or more sub-devices, one or more applications, one or more software programs, one or more hardware devices, one or more firmware programs, one or more application versions, one or more software versions, one or more hardware versions, one or more firmware versions, one or more associated users, etc., or any combination thereof) of the device(s) 114.

In those or other examples, the other data being managed by the pupil related characteristics management system 102 can include camera related data (e.g., data associated with, and/or identifying, at least one corresponding device of the camera(s) 116 (e.g., data associated with, and/or identifying, one or more of serial numbers, details, names, light source versions and/or types, camera versions and/or types, calibration dates, calibration types, manufacturing dates, ship dates, creation dates, version dates, expiration dates, power levels, etc., or any combination thereof). In those examples, the camera related data can be associated with one or more components, one or more sub-devices, one or more applications, one or more software programs, one or more hardware devices, one or more firmware programs, one or more application versions, one or more software versions, one or more hardware versions, one or more firmware versions, one or more associated users, etc., or any combination thereof) of the camera(s) 116.

Although the device related data and the camera related data can be separate from one another, as discussed above in the current disclosure, it is not limited as such. In some examples, at least one of the device related data, the camera related data, and/or user related data (e.g., data associated with names, addresses, account, medical history, etc., of one or more users of the device(s) 114, the camera(s) 116, or any combination thereof) can be separate from one another and/or combined in any way with each other. In those or other examples, any of the different types of data associated with any of the device(s) 114, the camera(s) 116, any users of the device(s) 114, and/or any users of the camera(s) 116, can be integrated together and managed in a similar way as any of the individual types of data for purposes of performing any techniques as discussed herein.

In some examples, various numbers of flashes of lights can be utilized for collection of the sensor data. For instance, any number of multi-flash based sensor data (e.g., sensor data based on one or more flashes of light) can be included in the sensor data received by the pupil related characteristics management system 102. In some examples, multi-flash based sensor data (e.g., sensor data generated based on multiple flashes of light) can be included in the sensor data.

In some cases, the pupil related characteristics management system 102 can utilize the dataset(s) (e.g., the portion (s) of the pupillary data) to identify, without performing intervening measurements, the pupil characteristics information, which can include the pupillary activity curve(s) (e.g., the pupil response curve(s)). The pupil characteristics information can be utilized to identify one or more classifications based on the pupillary data.

In some examples, the classification(s) can include one or more classifications (e.g., one or more current classification (s)) being analyzed, one or more classifications (e.g., one or more training classifications) previously identified and analyzed utilizing user input for purposes of training the ML model(s), and/or one or more other classifications of other types. In some examples, the training dataset used to train the ML model(s) described herein can include features and labels. However, the training dataset may be unlabeled, in some examples. Accordingly, the ML model(s) described herein may be trained using any suitable learning technique, such as supervised learning, unsupervised learning, semi-supervised learning, reinforcement learning, and so on. The features included in the training dataset can be represented by a set of features, such as in the form of an n-dimensional feature vector of quantifiable information about an attribute of the training dataset.

In various implementations, the classification(s) (e.g., the current classification(s), the training classification(s), etc.) can include one or more "normal" classifications, one or more physiological condition related classifications, and/or one or more other classifications of other types. In some examples, the "normal" classification(s) can include one or more classifications for which one or more physiological conditions (e.g., one or more selected physiological conditions and/or one or more predetermined physiological conditions) have not been identified. In those or other examples, the physiological condition related classification(s) can include one or more classifications for which one or more physiological conditions (e.g., one or more selected physiological conditions and/or one or more predetermined physiological conditions) have been identified.

The pupil related characteristics management system 102 can utilize the dataset(s) (e.g., the portion(s) of the pupillary data) and the pupil characteristics information to identify physiological condition information. In some examples, the dataset(s) can be analyzed, utilizing the pupil related data management component(s) 108, the pupil response curve data management component(s) 110, and/or the ML model component(s) 112 to generate the physiological condition information. For instance, with examples in which the ML model component(s) 112 are utilized to analyze the dataset (s), the ML model component(s) 112 can provide the dataset (s) as input to the ML model(s). Operation of the ML model component(s) 112 can include analyzing, via the ML model (s), the dataset(s) to output, by the ML model(s), the physiological condition information.

In some examples, one or more baselines can be identified, individual ones of the baseline(s) representing corresponding known physiological curves without at least one of the physiological conditions. The baselines can be identified via one or more baseline tags, and the baseline(s) can be stored with the baseline tag(s) as a portion of library data (e.g., one or more corresponding database files) in one or more library databases.

Although various types of data can be stored in the database(s), as discussed above in the current disclosure, it is not limited as such. In some examples, the data being stored can include any type of data (e.g., the sensor data, any of the data included therein, the pupillary data, any of the data included therein, any other data related to and/or utilized along with the sensor data and/or the pupillary data, and/or one or more of any other types of data). In those or other examples, the data of any type can be stored in the database(s), one or more libraries of any types associated with and/or stored by the database(s), one or more libraries stored in any other way, one or more other types of storage mechanisms of any type, or any combination thereof. For instance, the library(ies) can include one or more curve libraries (e.g., one or more libraries including the pupillary activity curve data (e.g., the pupil response curve(s)), one or more pupil response curve libraries (e.g., one or more libraries including the pupil response curves), any other types of libraries, or any combination thereof.

In some cases, the dataset(s) can be collected by calibrating the pupillary activity curves. The pupillary activity curves can be calibrated by collecting light level data associated with one or more environments (e.g., one or more environments including one or more users with which the sensor data is associated) in which the sensor data is captured. Video data can be collected representing the pupillary activity. The video data can be transformed into time series curve data associated with one or more changes of one or more diameters of individual ones of at least one pupil of a user over time. In some examples, the dataset(s) can be collected as the pupillary activity curve(s) (e.g., the pupil response curve(s)) based on the light level data, the video data, and the time series curve data.

In various implementations, the ML model(s) can be utilized to perform the comparison(s) between the current pupillary activity data (e.g., the current pupil response curve data) and the training pupillary activity data (e.g., the training pupil response curve data). For instance, with examples in which the current pupil response curve data is compared with the training pupil response curve data, the ML model(s) can be utilized to compare the current pupil response curve(s) in the pupil response curve data and one or more training pupil response curves in the training pupil response curve data.

In various cases, one or more new ML models can be added and/or included as part of the ML model(s) in the ML model component(s) 112 on an ongoing basis. For example, the new ML model(s) can be added dynamically as one or more identifications (e.g., one or more discoveries, one or more determinations, one or more generations, one or more selections, one or more modifications, etc., or any combination thereof) of corresponding curves associated with physiological conditions. New discoveries can be utilized to identify new ways to perform different methods of diagnosis, as new information is collected, studied, and utilized to update the ML model component(s) 112.

The ML model component(s) 112 can include the ML model(s), which can include one or more classification models. The classification model(s), for example, can be utilized to classify the pupil response curve(s) based on analysis by the ML model(s). In some cases, the classification model(s) can represent one or more mathematically generated classifications based on the physiological conditions.

The ML model(s) used by the techniques and systems described herein may represent a single model or an ensemble of base-level ML models, and may be implemented as any type of ML model. For example, suitable ML models for use by the techniques and systems described herein include, without limitation, neural networks (e.g., generative adversarial networks (GANs), deep neural networks (DNNs), recurrent neural networks (RNNs), etc.), tree-based models (e.g., eXtreme Gradient Boosting (XGBoost) models), support vector machines (SVMs), kernel methods, random forests, splines (e.g., multivariate adaptive regression splines), hidden Markov model (HMMs), Kalman filters (or enhanced Kalman filters), Bayesian networks (or Bayesian belief networks), multilayer perceptrons (MLPs), expectation maximization, genetic algorithms, linear regression algorithms, nonlinear regression algorithms, logistic regression-based classification models, or an ensemble thereof. An "ensemble" can comprise a collection of ML models whose outputs (predictions) are combined, such as by using weighted averaging or voting. The individual ML models of an ensemble can differ in their expertise, and the ensemble can operate as a committee of individual ML models that is collectively "smarter" than any individual ML model of the ensemble.

Although the ML model(s) can be utilized to analyze the pupillary data, as discussed above in the current disclosure, it is not limited as such. In some examples, any of one or more types of models, which can possibly include any of the ML model(s), can be utilized in a similar way as the ML model(s) for purposes of implementing any of the techniques as discussed throughout the current disclosure. In those or other examples, the model(s) include one or more models of various types, which can include one or more data algorithm models of various types, one or more artificial intelligence (AI) models of various types, one or more other models, or any combination thereof. In those or other examples, any of the ML models of various types can be, and/or include, any of the ML model(s) and/or one or more models of other types.

Although various types of model(s) (e.g., the ML and/or AI model(s) can be utilized to analyze the pupillary data, as discussed above in the current disclosure, it is not limited as such. In some examples, the model(s) can include one or more ML models that are unsupervised and/or one or more ML models that are supervised. For instance, with examples including the unsupervised ML model(s), the model(s) can include one or more principal component analysis (PCA) ML models, one or more K-means clustering ML models, one or more mean shift algorithm ML models, one or more density-based spatial clustering of applications with noise (DBSPCAN) ML models, one or more k-nearest neighbors (KNN) ML models, one or more hierarchal clustering ML models, one or more anomaly detection ML models, one or more neural networks ML models, one or more independent component analysis ML models, one or more apriori algorithm ML models, one or more other types of unsupervised ML models, or any combination thereof. Alternatively or additionally, with examples including the supervised ML model(s), the model(s) can include one or more random forest algorithm ML models, one or more decision tree algorithm ML models, one or more logistic regression algorithm ML models, one or more support vector machine algorithm ML models, one or more other types of supervised ML models of various types, or any combination thereof.

In those or other examples, the model(s) (e.g., the ML model(s)) can include one or more large language models (e.g., the ML model(s) can include various types of ML models, including the large language models). For instance, the large language model(s) can be utilized for analyzing of the pupil response curve(s). In various cases, the large language model(s), alternatively or additionally to one or more other models (e.g., any of the model(s), as discussed herein), can be utilized to identify the one or more classification(s) of the pupil response curves and synthesize clinical information provided to the model in combination with the pupil response curves to generate a clinical status analysis.

Performing, by the large language model(s), of the classification to identify the pupil response curves classification (s) can include analyzing, via the large language model(s), the pupil response curve(s) to identify one or more diseases are best fits for the pupil response curve(s). The large language model(s), for example, "answer a question" of what disease(s) are best fits with the pupil response curve(s) (e.g., the PLR curve(s)) for individual ones of the patient(s) using the computing device(s) 114 to capture the sensor data.

In some cases, one or more baselines can be identified (e.g., determined, generated, selected, modified, etc., or any combination thereof). Individual ones of the training pupil response curve(s) can be identified as the corresponding baseline(s).

In some examples, individual ones of the baseline(s) can be utilized as corresponding representative curves, based on consolidation of pupillary activity data comprising the pupillary activity curve(s) (e.g., the training pupillary activity curves) (e.g., the training pupil response curve(s)). For instance, individual ones of the baselines can represent corresponding known physiological curves without at least one of the physiological condition(s). The baselines can be identified via one or more baseline tags, and the baseline(s) can be stored with the baseline tag(s) as a portion of library data in one or more library databases.

For example, a baseline can be utilized as a representative curve associated with a "normal" diagnosis. In those or other examples, individual ones of the baseline(s) can be utilized as corresponding representative curves, which are not associated with corresponding physiological conditions (e.g., a baseline can be utilized as a representative curve that is not associated with any physiological condition and/or a diagnosis of a corresponding physiological condition).

The ML model(s) can utilize the classification information (e.g., the classification(s)) to identify the physiological condition information based on the comparison(s). For example, at least one of the classification(s) associated with the current pupil response curve(s) can be identified based on the comparison(s) between the current pupil response curve(s) and the training pupil response curve(s). The identified at least one classification, which may be associated with at least one of the physiological condition(s), can be utilized to identify the current pupil response curve(s) as being associated with the at least one physiological condition.

In some examples, the current pupil response curve(s) being identified as being associated with the at least one physiological condition can be based on how similar the current pupil response curve(s) is to the training pupil response curve(s). By utilizing the training pupil response curve(s) being identified as being associated with the training classification(s), at least one of the training classification (s) (e.g., at least one training classification associated with at least one physiological condition) can be identified as at least one current classification (e.g., at least one current classification associated with the at least one physiological condition). By utilizing the training pupil response curve(s) and the training classification(s) to analyze the current pupil response curve(s) and to identify the at least one current physiological condition, the current pupil response curve(s) can be identified as being associated with the at least one current physiological condition.

The physiological condition information can be identified accurately and efficiently by utilizing the multi-flash light data. In contrast to conventional technology that is limited to sensor data being generated based on a single flash of light, the flexibility and utilization of sensor data based on various numbers of flashes of light as discussed throughout the current disclosure beneficially provides sensor data that is more accurate, and that is usable for identifying larger numbers of physiological conditions. By increasing the types of light, which can include light with various numbers of flashes of light utilized to collect the sensor data, the pupil related characteristics management system 102 can identify, more efficiently and more effectively, larger numbers and/or larger varieties of physiological conditions.

However, although multi-flash based sensor data can be included in the sensor data, as discussed above in the current disclosure, it is not limited as such. In some examples, single-flash based sensor data (e.g., sensor data generated based on a single flash of light) can be included in the sensor data.

In some examples, the type(s) of light may include "non-specialized light" (e.g., light not associated with a measurement and/or medical device), "specialized light" (e.g., light associated with a measurement and/or medical device), ambient light (e.g., "overall illumination" in a space, such as a room, an area, etc., which may include "uniform" light and/or a combination of light, including direct and/or indirect light, associated with one or more sources), indirect light (e.g., light being reflected by at least one object between any light source and any user), direct light (e.g., light not being reflected by any object between any light source and any user). In those or other examples, the type(s) of light may include steady light (e.g., light that does not include any interruptions and/or moments in which transmission of the light ceases), one or more light flashes (e.g., one or more flashes of light) (e.g., one or more pulses of light), or one or more other types of light, or any combination thereof. In some examples, the light may have one or more of various levels of one or more characteristics, respectively (e.g., one or more of brightness, intensity, duration, etc., or any combination thereof, respectively).

In various implementations, utilizing various ones of the type(s) of light has benefits in contrast to utilizing various other ones of the type(s) of light. For instance, with examples in which "non-specialized" light (e.g., light being emitted that is not associated with, and/or part of, any operation utilized to gather sensor data based on any reflection of light by any portion of a user) (e.g., ambient light) is utilized as the emitted light (e.g., emitted light), the sensor data can be captured by the camera(s) 116 without requiring control of emission (e.g., "specialized" emission) (e.g., pupil related device light) (e.g., pupillometer light) (e.g., pupil reflex device light) (e.g., light emitted for purposes of obtaining pupil response data) of light (e.g., one or more flashes of light, steady light, etc.). For example, the "non-specialized" light (e.g., light not emitted by a pupil related device) (e.g., light not emitted by a pupillometer) (e.g., light not being emitted by a pupil reflex device) (e.g., light not being emitted for purposes of obtaining pupil response data) can be associated with an absence of emission of "specialized" light (e.g., measurement-oriented light, light generated and/or emitted for purposes of capturing the sensor data, etc.) by the computing device(s) 114, the camera(s) 116, or any combination thereof).

In such an instance, with examples in which the "non-specialized" light is utilized, the sensor data can be captured by the camera(s) 116 without requiring emission of "specialized" light (e.g., one or more flashes of light, steady light, etc.) by any device. The utilization of the "non-specialized" light can include utilization of light by any of the device(s) (e.g., computing device(s) 114, the camera(s) 116, any of the other device(s), or any combination thereof) during "normal" operation (e.g., during at least one of any type of operation of the device(s) that is not associated with, triggered for, utilized for, and/or related to, generating and/or capturing sensor data).

In some examples, by utilizing the light with the flash(es), (e.g., the flashes of light enable pupil diameter changes to be identified in response to the flash(es) as "external stimuli"). In those or other examples, by utilizing the light without the flash(es), (e.g., absence of the flashes of light enable pupil diameter changes to be identified in response to other light as "internal stimuli").

In various implementations, with examples in which "non-specialized" light is utilized as the emitted light, the sensor data can be captured by the camera(s) 116 without "alerting" (e.g., indicating, informing, warning, distracting, bothering, interrupting, etc.) individual ones of the user(s). In some examples, by utilizing "non-specialized" light (e.g., ambient light) (e.g., light emitted from various sources) (e.g., sunlight, light emitted by the computing device(s) 114, light emitted by the camera(s) 116, light emitted by various other devices, etc., or any combination thereof) (e.g., light emitted as part of a "normal" operation, or any other type of operation) (e.g., light emitted by one or more displays, one or more indicators, etc., or any combination thereof, included in any of the computing device(s) 114 and/or any of the camera(s) 116, etc., or any combination thereof), the sensor data can be generated (e.g., captured) without "alerting" the user(s).

In those or other examples, the sensor data can be generated (e.g., captured) without any of one or more visual indications to the user(s) regarding any operations associated with the capturing of the sensor data. For instance, the sensor data being generated without any of the visual indication(s) may be utilized for "passive" generation (e.g., capturing) of the sensor data. In various cases, the sensor data being generated without the visual indication(s) may include an absence of all visual indication(s) associated with the generating of the sensor data. Alternatively, the sensor data being generated without the visual indication(s) may include individual ones of the visual indication(s) below corresponding threshold visual indication(s) (e.g., at least one threshold visual indication based on a threshold perceptibility associated with perceptibility by an "average" or "typical" user being likely to perceive any occurrence of any visual indication, a threshold visual capability associated with a visual capability of an "average" or "typical" user being physiologically capable of identifying any visual indication, a threshold distractibility associated with a level by visual indication likely to distract an "average" or "typical" user, etc., or any combination thereof).

In some cases, the light (e.g., the emitted light, the reflected light, the received light, etc.) may include any of one or more types of light. For instance, individual ones of the type(s) of light may ultimately originate from (e.g., being originally emitted by) any number of corresponding sources (e.g., a corresponding group of at least one of the source(s)).

In some cases, the light (e.g., the emitted light, the reflected light, the received light, etc.) may include light of one or more various wavelengths of light. For example, individual ones of the portion(s) of the light may have one or more corresponding wavelengths. The wavelength(s) may include any wavelength associated with visible light, any wavelength associated with infrared light, any other wavelength associated with any other type of light, or any combination thereof.

In some examples, with respect to the light having the various type(s) of the characteristic(s) (e.g., the one or more of the brightness, the intensity, the duration, any of one or more other characteristics of one or more other types, or any combination thereof), individual ones of the characteristic(s) may increase for a corresponding period of time of one or more periods of time and/or decrease for a corresponding period of time of one or more periods of time. For instance, the period(s) may include any number of periods during which individual ones of the characteristic(s) increase and/or any number of periods during which individual ones of the characteristic(s) decrease. In some examples, in a similar way as for the periods of time, individual ones of the characteristic(s) may increase for one or more corresponding intervals associated with any instances (e.g., occurrences, actions, behaviors, etc.) of any types and/or decrease for one or more corresponding intervals associated with any instances (e.g., occurrences, actions, behaviors, etc.) of any types.

In some implementations, the light may have individual ones of the characteristic(s) with one or more varying levels, respectfully, that are undulating, periodic (e.g., periodically changing), aperiodic (e.g., periodically changing), random (e.g., randomly changing), etc., or any combination thereof. In some examples, individual ones of the characteristic(s) may have at least one of the varying level(s) with one or more identical peaks (e.g., peaks with identical values) or with one or more non-identical peaks (e.g., peaks with non-identical, or differing values). In those or other examples, individual ones of the characteristic(s) may have at least one of the varying level(s) with one or more identical transitions (e.g., transitions between peaks with identical slopes) or with one or more non-identical transitions (e.g., transitions between peaks with non-identical (e.g., differing) slopes).

In some cases, the light may include one or more portions light of one or more categories, respectively. For example, individual ones of the category(ies) may include at least one of the type(s) of light, at least one of the characteristic(s), at least one of the level(s) of individual ones of the characteristic(s), at least one of the wavelength(s), etc., or any combination thereof.

In some examples, a portion of one or more portions of the light (e.g., the light that is emitted, reflected, and received) may be of a category, which can include at least one type of light (e.g., at least one of the type(s) of light), at least one characteristic (e.g., any of the characteristic(s)), at least one level (e.g., at least one of the level(s) of individual ones of the characteristic(s), at least one wavelength (e.g., at least one of the wavelength(s)), etc., or any combination thereof.

In those or other examples, another portion of the light (e.g., another portion of the light that is emitted, reflected, and received) may be of another category, which can include at least one other type of light (e.g., at least one other of the type(s) of light), at least one other characteristic (e.g., any of the characteristic(s)), at least one other level (e.g., at least one other of the level(s) of individual ones of the characteristic(s), at least one other wavelength (e.g., at least one other of the wavelength(s)), etc., or any combination thereof.

In various cases, any of the portion(s) of the light may be associated with operation of (e.g., transmission, emission, etc. by) at least one of the source(s), which may be the same as, or different from, operation of (e.g., transmission, emission, etc. by) at least one other of the source(s) with which any other of the portion(s) of the light may be associated. In those or other examples, any of the portion(s) of the light may have at least one aspect of any category (e.g., any of the at least one type of light, any of the at least one characteristic, any of the at least one level, any of the at least one wavelength, any at least one other aspect, or any combination thereof) that is the same as, or different from, at least one other corresponding aspect of any other category (e.g., any of the at least one other type of light, any of the at least one other characteristic, any of the at least one other level, any of the at least one other wavelength, any at least one other aspect, or any combination thereof) of any other of the portion(s) of the light.

In various implementations, individual ones of the portion (s) the light may be of one or more corresponding amounts (e.g., one or more corresponding portions, one or more corresponding proportions, one or more corresponding percentages, etc., or any combination thereof) of the light. For example, individual ones of the amounts may be associated with corresponding points (e.g., instances, moments, etc.) in time.

In some cases, individual ones of the amounts may be associated with corresponding intervals and/or time periods (e.g., a group of points (e.g., instances, moments, etc.) in time). For instance, with examples in which individual ones of the amount(s) of the portion(s) of light are associated with the corresponding interval(s) and/or time period(s) (e.g., an amount of a portion of the light associated with at least one consecutive point in time), individual ones of the amount(s) may include an average of at least one of one or more other amounts of at least one of the portion(s) of light associated with corresponding point(s) of time. In such an instance, individual ones of the amounts may include corresponding averages of corresponding groups (e.g., individual ones of the groups being associated with levels of intensity, brightness, duration, or any combination thereof, respectively, of the corresponding portion(s) of light).

For instance, with examples in which an amount of a portion of the light of a category is “greater” than another amount of another portion of the light of another category, the portion of light of the category (e.g., a category that includes no flashes of light) may be “stronger” than another portion of light of another category (e.g., a category that includes one or more flashes of light). In such an instance, the portion of light of the category being “stronger” may have at least one levels of individual ones of the characteristic(s) (e.g., at least one brightness, intensity, duration, etc., or any combination thereof, respectively) that is greater than at least one other corresponding level of individual ones of the characteristic(s) (e.g., at least one of brightness, intensity, duration, etc., or any combination thereof, respectively) of the other portion of light of the other category, respectively.

In some examples, the portion of the light of the category (e.g., a category that includes no flashes) being “stronger” may correspond to the portion of the light having a relatively greater impact on the sensor data in comparison to the other portion of the light of the other category (e.g., the other category that includes the flash(es)). For instance, the amount of the portion of the light having the relatively greater impact on the sensor data may be due to the amount being greater than a threshold amount (e.g., a first threshold amount). In those or other examples, the other portion of the light of the other category (e.g., the other category that includes the flash(es)) being “weaker” may correspond to the other portion of the light having a relatively lesser impact on the sensor data. In such an instance, the other amount of the other portion of the light having the relatively lesser impact on the sensor data may be due to the other amount being lower than a threshold amount (e.g., the first threshold amount and/or a second threshold amount).

In some instances, the first threshold amount may correspond to an amount of a reaction (e.g., a physiological reaction to a size, a diameter, etc.) of a pupil that is measurable (e.g., identifiable, detectable, etc.) by an accuracy that is greater than a threshold accuracy (e.g., a first threshold accuracy). In those or other examples, the second threshold amount may correspond to an amount of a reaction of a pupil that is not measurable (e.g., not identifiable, not detectable, etc.) by an accuracy that is greater than a threshold accuracy (e.g., the first threshold accuracy or a second threshold accuracy).

Although one or more of various metrics associated with various characteristics (e.g., the size, the diameter, etc.) of one or more pupils are identified, such as based on the sensor data, and/or, for instance, are utilized to identify the pupillary activity curve(s) (e.g., the pupil response curve(s)), as discussed above in the current disclosure, it is not limited as such. In some examples, one or more metrics of any type and/or one or more parameters of any type, which can be associated with one or more characteristics of any type, and which can include one or more near point convergence metrics, one or more saccades metrics, one or more pursuit metrics, one or more of other types of metrics, or any combination thereof, can be identified and utilized in a similar way as for a size metric and/or a diameter metric for purposes of implementing any of the techniques as discussed herein.

In various implementations, the metric(s) can include, alternatively or additionally to any of the metric(s) as discussed above, one or more metrics of various other types. In some examples, the metric(s) can include one or more metrics associated with pupil latencies, pupil constriction velocities, pupil dilation velocities, changes in pupillary diameter, times to percent pupil dilation, times to percent pupil constriction, any other types of metrics, or any combination thereof.

For example, a time to percent pupil dilation can include an amount of time between an occurrence of a first pupil diameter (e.g., a minimum diameter achieved based on the pupil being exposed to one or more types of light, such as ambient light, a light stimulus, etc., and/or one or more images, prior to a time at a beginning of a period of time, such as a test period) at a first time (e.g., the time at the beginning of the test period at which the type(s) of light are removed from a line of site of a subject) (e.g., the time at the beginning of the test period at which the image(s) are removed from a line of site of a subject), and an occurrence of a second pupil diameter (e.g., a relatively larger diameter) at a second time (e.g., a time at an ending of the test period).

In some instances, the second pupil diameter can include a diameter associated with a 75 percent re-dilation to a baseline pupil diameter. In those or other instances, the baseline pupil diameter can be associated with a diameter of the pupil represented by the baseline curve at the second time (e.g., an end of the baseline curve).

In such an example or another example, a time to percent pupil constriction can include an amount of time between a first diameter (e.g., a baseline pupil diameter) of a pupil to a second diameter (e.g., a relatively smaller diameter) of a pupil. In various instances, the time to percent pupil constriction can include an amount of time for a pupil to change from having a first diameter (e.g., a diameter of the pupil prior to an onset of light stimulus, a placement of an image in front of a subject, etc.) (e.g., a baseline pupil diameter) at a first time (e.g., a time at which the onset of the light stimulus is performed, the placement of the image in front of the subject is performed, etc.) to a second diameter (e.g., a diameter at 50 percent pupil constriction in response to the light stimulus being performed, the image placement, etc.).

Although various types of scenarios are utilized to perform the test(s) and/or identify the metric(s), as discussed above in the current disclosure, it is not limited as such. In some examples, any of one or more of metrics of various types are identifiable based on any of one or more scenarios of various types (e.g., light stimuli, light removal, image placement, image removal, etc.) in a similar way as for any of the other metric(s) for purposes of implementing any of the techniques as discussed herein. For example, a bright light, a blinking light, a steady light, a pleasing image, a frightening image (e.g., being expected to cause a sympathetic autonomic nervous system response which would lead to pupil dilation), any of one or more other types of light and/or images, for example, being expected to lead to any of various types of pupil activity, can be utilized to produce one or more pupillary activity curves.

In various implementations, the metric(s) can include, alternatively or additionally to any of the metric(s) as discussed above, one or more vestibulo-ocular metrics, one or more oscillation metrics, one or more nystagmus metrics, one or more oculomotor metrics, one or more eye tracking metrics, one or more reaction time metrics, one or more of any other types of metrics, or any combination thereof. Any of the metric(s) can be utilized in a similar way as for a size metric and/or a diameter metric for purposes of implementing any of the techniques as discussed herein.

Although the amount of the portion of the light of the category may be relatively greater than the amount of the other portion of the light of the other category, as discussed above in the current disclosure, it is not limited as such. In some examples, the amount of the portion of the light of the category may include a total amount of the light based on the portion of the light of the category including an entire portion of the light, and the light including no other portion. For instance, with examples in which the light includes the portion of light (e.g., ambient light, steady light, etc., or any combination thereof) with no flashes and/or with no light being emitted (e.g., output) by the computing device(s) 114 and/or the camera(s) 116, the light may include no other portion of light (e.g., the light may include no portion of flashing light and/or no light being emitted by the computing device(s) 114 and/or the camera(s) 116).

Alternatively, for instance, with examples in which the light includes the portion with the flash(es), the light may include no other portion of light. In such an instance, the light may include no portion of non-flashing light (e.g., the light may be devoid of any ambient light, steady light, etc., or any combination thereof).

Although the terms "steady light" and "ambient light" may be utilized, for purposes of simplicity and ease of explanation, to refer to light that includes steady light and/or ambient light, as well as some relatively smaller portion of flashing light (e.g., flashing light of a smaller degree), as discussed above with respect to the current disclosure, it is not limited as such. Any of the terms "steady light" and "ambient light" as discussed throughout the current disclosure may be utilized to refer to light that includes only the light without flashes and/or the ambient light, such as light that does not include any portions of flashing light. In some examples, the terms "steady light" and "ambient light" as discussed throughout the current disclosure may be utilized to refer to light including a portion of flashing light that may be disregarded as being of a negligible effect (e.g., due to individual ones of the level(s) of the intensity, the brightness, the duration, or any combination thereof, respectively, being less than corresponding thresholds).

Although the terms "flashing light" may be utilized, for purposes of simplicity and ease of explanation, to refer to light that includes flashing light, as well as some relatively smaller portion of steady light (e.g., some portion of steady light of correspondingly smaller levels of intensity, the brightness, the duration, or any combination thereof, respectively) and/or some relatively smaller portion of ambient light (e.g., some portion of ambient light of correspondingly smaller levels of intensity, the brightness, the duration, or any combination thereof, respectively), as discussed above with respect to the current disclosure, it is not limited as such. The term "flashing light" as discussed throughout the current disclosure may be utilized to refer to light that includes only the light with flashes, such as light that does not include any portions of steady light and/or ambient light. In some examples, the terms "flashing light" as discussed throughout the current disclosure may be utilized to refer to light including a portion of steady light and/or a portion of ambient light that may be disregarded as being of a negligible effect (e.g., due to individual ones of the level(s) of the intensity, the brightness, the duration, or any combination thereof, respectively, being less than corresponding thresholds).

In various implementations, the light (e.g., one or more light beams) (e.g., one or more rays of light) that is reflected by the user(s) may be emitted by one or more sources (or "light source(s)"). For instance, with examples in which a single source of light emits the light, as emitted light, to a user, a portion (e.g., a partial portion or an entire portion) of the emitted light (e.g., the emitted light beam(s)) (e.g., the emitted light ray(s)) is received by the user (e.g., any of the portion(s) of the user). In another instance, with examples in which more than one source of light (e.g., light sources) emits the light, as emitted light, to a user, a portion (e.g., a partial portion or an entire portion) of the emitted light (e.g., at least one of the light beam(s) being emitted by individual ones of the light sources) (e.g., the emitted light ray(s) being emitted by individual ones of the light sources) is received by the user (e.g., any of the portion(s) of the user).

In some implementations, the captured data may be based on a portion (e.g., a partial portion or an entire portion) of the light (e.g., at least one of the light beam(s) associated with at least one of the portion(s) of light) (e.g., at least one of the ray(s) associated with at least one of the portion(s) of light) being reflected, as reflected light, by one or more portions of individual ones of one or more users (e.g., at least one of the user(s)). For example, individual ones of the at least one of the light beam(s) and/or individual ones of the at least one of the ray(s) of light may be reflected by any portion of a user.

In some examples, the captured data may be based on the light (e.g., at least one of the portion(s) of light) being reflected, as the reflected light, by one or more eyes of individual ones of the user(s). In those or other examples, the captured data may be based on the light being reflected, as the reflected light, by individual ones of one or more portions (e.g., one or more pupils) of corresponding eyes. In those or other examples, the captured data may be based on the reflected light being received by individual ones of the camera(s) 116 (e.g., at least one of the camera(s) 116).

Figure 2:
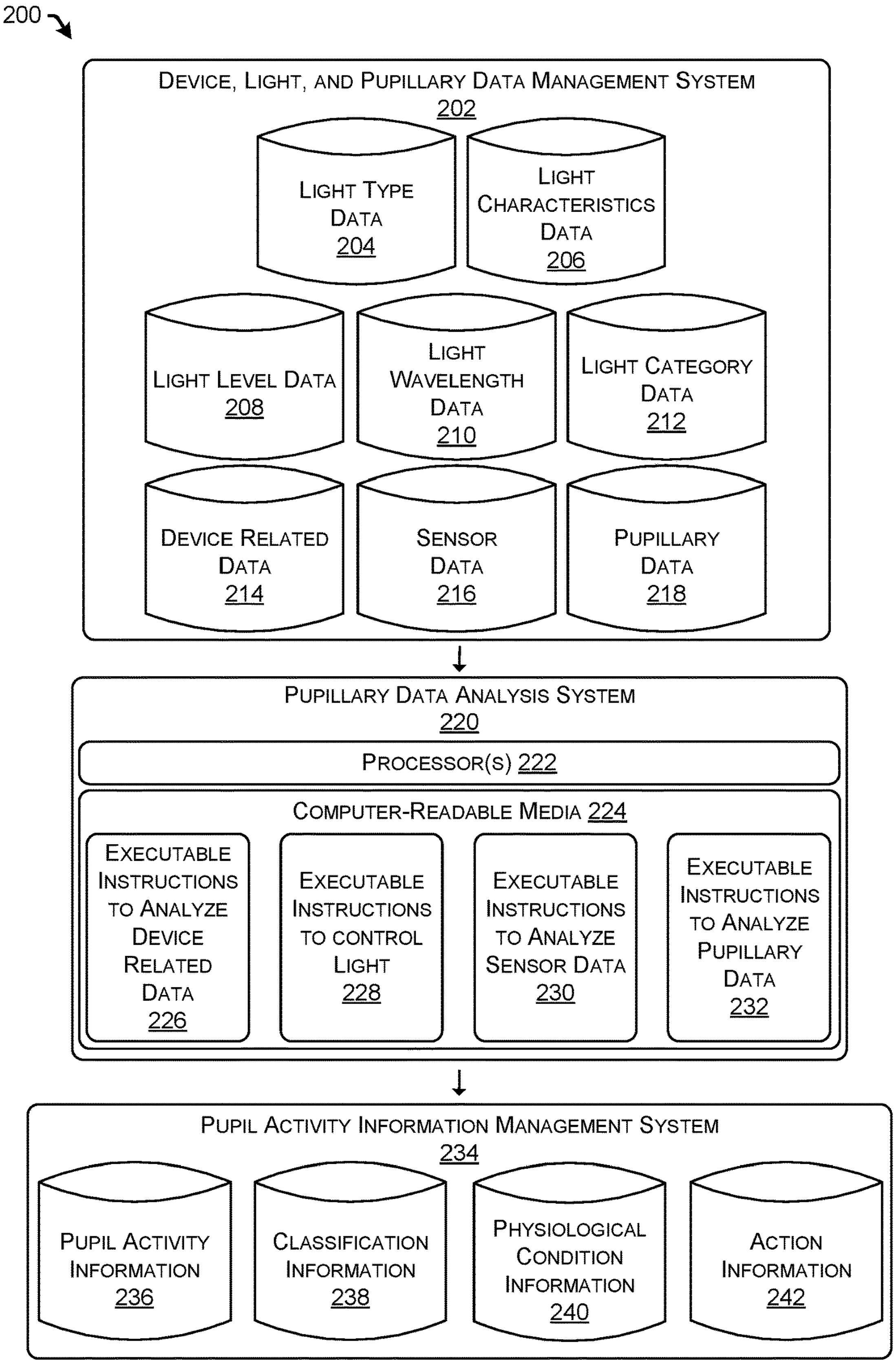
FIG. 2 depicts example systems for performing pupillary curve morphology and diagnosis management.

FIG. 2 depicts example systems 200 for performing pupillary curve morphology and diagnosis management. In various implementations, the systems 200 can include a device, light, and pupillary data management system 202. The device, light, and pupillary data management system 202 can be utilized to manage light type data 204, light characteristics data 206, light level data 208, light wavelength data 210, light category data 212, device related data 214, sensor data 216, pupillary data 218, and/or one or more types of other data of various types (e.g., camera related data, user related data, etc.).

In some examples, the light type data 204, the light characteristics data 206, the light level data 208, the light wavelength data 210, the light category data 212, the device related data 214, the sensor data 216, and/or the pupillary data 218 can be implemented as one or more corresponding types of data (e.g., the light type data, the light characteristics data, the light level data, the light wavelength data, the light category data, the device related data, the sensor data, and/or the pupillary data, respectively), as discussed above with reference to FIG. 1.

In various implementations, the systems 200 can include a pupillary data analysis system 220. The pupillary data analysis system 220 can include one or more processors 222 and one or more computer-readable media 224.

In some examples, the pupillary data analysis system 220 can be separate from the device, light, and pupillary data management system 202. In alternative examples, any portion (e.g., a partial portion or an entire portion) of the pupillary data analysis system 220 can be combined together, and/or integrated, with any portion (e.g., a partial portion or an entire portion) of the device, light, and pupillary data management system 202.

In some examples, the pupillary data analysis system 220, the processor(s) 222, and the computer-readable media 224 can be implemented by, and/or be utilized to implement, one or more portions of the pupil related characteristics management system 102, the processor(s) 104, and the computer-readable media 106, respectively, as discussed above with reference to FIG. 1, and/or any of the operations associated therewith.

Although the pupillary data analysis system 220, the processor(s) 222, and the computer-readable media 224 can be implemented by, and/or be utilized to implement, the portion(s) of the pupil related characteristics management system 102, the processor(s) 104, respectively, as discussed above with reference to FIG. 1, as discussed above in the current disclosure, it is not limited as such. In some examples, a portion (e.g., a partial portion or an entire portion) of the pupillary data analysis system 220 can include any portion (e.g., a partial portion or an entire portion) of the pupil related characteristics management system 102. In those or other examples, a portion (e.g., a partial portion or an entire portion) of the pupil related characteristics management system 102 can include any portion (e.g., a partial portion or an entire portion) of the pupillary data analysis system 220.

In some examples, the computer-readable media 224 includes executable instructions to analyze device related data 226, executable instructions to control light 228, executable instructions to analyze sensor data 230, and/or executable instructions to analyze pupillary data 232. In various examples, the executable instructions to control light 228 can be utilized to cause emission (e.g., output) of light (e.g., light output in any way, as discussed above with reference to FIG. 1).

In various cases, the executable instructions to analyze device related data 226 can be utilized to perform one or more operations to identify (e.g., determine, generate, select, modify, etc., or any combination thereof) various types of device related data (e.g., the device related data 214, which can include data associated with the computing device(s) 114, the camera(s) 116, and/or any other devices of various types, as discussed above with reference to FIG. 1).

In some cases, the executable instructions to analyze device related data 226 can be utilized to transmit, via one or more transceivers, one or more signals to the one or more devices (e.g., the computing device(s) 114, the camera(s) 116, and/or any other devices of various types, as discussed above with reference to FIG. 1). In various examples, at least one of the signal(s) can be transmitted based on user input (e.g., user input to the pupillary data analysis system 220).

In some examples, transmitting of the signal(s) can be utilized to control, request, cause, etc., or any combination thereof, the computing device(s) 114 and/or the camera(s) 116 to transmit the device related data 214. In those or other examples, one or more signals including the device related data 214 can be transmitted by the computing device(s) 114 and/or the camera(s) 116, to the pupillary data analysis system 220 based on the signal(s) transmitted to the computing device(s) 114 and/or the camera(s) 116.

In some implementations, transmitting the signal(s) including the device related data 214 by the computing device(s) 114 and/or the camera(s) 116 can be automated. For example, at least one of the signal(s) requesting the device related data 214 can be periodically transmitted by the pupillary data analysis system 220. In some examples, at least one of the signal(s) can be transmitted by the pupillary data analysis system 220 at one or more scheduled intervals. In some examples, at least one of the signal(s) can be transmitted by the pupillary data analysis system 220 at one or more times (e.g., one or more moments in time).

Any of the various ways of transmitting the signal(s) by the pupillary data analysis system 220 may be based on, for instance, user input. In some examples, one or more selections received via user input to the pupillary data analysis system 220 can be identified. In those or other examples, at least one of the selection(s) can include data utilized to transmit the signal(s) periodically, at the scheduled interval (s), at the time(s), at one or more other scheduled times, based on one or more triggers (e.g., based on one or more user input of other types, based on one or more occurrences of one or more operations of other types performed by the pupillary data analysis system 220, etc., or any combination thereof.

In various cases, transmitting of the signal(s) including the device related data 214, by the computing device(s) 114 and/or the camera(s) 116, can be performed based on the computing device(s) 114 and/or the camera(s) 116 transmitting the signal(s) without receiving any corresponding signal (s) from the pupillary data analysis system 220. For example, the computing device(s) 114 and/or the camera(s) 116 can periodically transmit the signals (e.g., the signal(s) including the device related data 214), at the one or more scheduled intervals, at one or more times, at one or more other scheduled times, based on one or more triggers (e.g., based on one or more user input of other types, based on one or more occurrences of one or more operations of other types performed by the computing device(s) 114 and/or the camera(s) 116, etc., or any combination thereof. In some examples, at least one of the signal(s) with the device related data 214 can be received from the computing device(s) 114 and/or the camera(s) 116 based on one or more selections received via user input to the computing device(s) 114 and/or the camera(s) 116.

In various examples, one or more portions of the device related data 214 can be identified by the computing device(s) 114 and/or the camera(s) 116, in combination with an of the operation(s) utilized to transmit the signal(s) with the device related data 214 to the pupillary data analysis system 220. In some cases, the at least one of the selection(s) received by the computing device(s) 114, the camera(s) 116, and/or the pupillary data analysis system 220 can be utilized to identify (e.g., determine, generate, select, modify, etc., or any combination thereof), and/or to triggering identifying of, one or more portions of the device related data 214. Alternatively or additionally, identifying (e.g., determining, generating, selecting, modifying, etc., or any combination thereof) of the portion(s) of the device related data 214 can be performed based on (e.g., triggered by) any of one or more other operations performed by of the computing device(s) 114, the camera(s) 116, and/or the pupillary data analysis system 220.

For example, identifying (e.g., determining, generating, selecting, modifying, etc., or any combination thereof) of the portion(s) of the device related data 214 can be automated (e.g., performed based on execution of software, applications, etc.). In some instances, identifying (e.g., determining, generating, selecting, modifying, etc., or any combination thereof) of the portion(s) of the device related data 214 can be based on one or more modifications of capabilities, equipment, programming, and/or any other aspects of the computing device(s) 114, the camera(s) 116, and/or the pupillary data analysis system 220.

In various implementations, the executable instructions to control light 228 can be utilized to perform one or more operations based on output provided via execution of the executable instructions to analyze device related data 226. In some cases, the executable instructions to control light 228 can be utilized to perform one or more operations utilized to identify (e.g., determine, generate, select, modify, etc., or any combination thereof) any data associated with light emitted by the device(s) (e.g., the computing device(s) 114, the camera(s) 116, and/or any other devices of various types, as discussed above with reference to FIG. 1).

In some examples, the operation(s) performed via the executable instructions to control light 228 can be utilized to obtain data (e.g., the sensor data 216) based on the light being emitted. In those or other examples, the operation(s) performed via the executable instructions to control light 228 can be utilized to obtain data (e.g., the sensor data 216, the pupillary data 218, etc., or any combination thereof) provided as input to one or more ML models (e.g., the ML model(s) as discussed above with reference to FIG. 1).

In some cases, the executable instructions to control light 228 can be utilized to transmit one or more signals (e.g., one or more request signals, one or more control signals, etc., or any combination thereof) to the one or more devices (e.g., the computing device(s) 114, the camera(s) 116, and/or any other devices of various types, as discussed above with reference to FIG. 1). In various examples, at least one of the signal(s) can be transmitted based on user input (e.g., user input to the pupillary data analysis system 220).

In some cases, transmitting of the signal(s) utilized to control and/or cause light emission (e.g., output) by the computing device(s) 114 and/or the camera(s) 116 can be automated. For example, at least one of the signal(s) can be transmitted periodically. In some examples, at least one of the signal(s) can be transmitted at one or more scheduled intervals. In some examples, at least one of the signal(s) can be transmitted at one or more times (e.g., one or more moments in time).

Any of the various ways of transmitting the signal(s) may be based on, for instance, user input. In some examples, one or more selections received via user input to the pupillary data analysis system 220 can be identified. In those or other examples, at least one of the selection(s) can include data utilized to transmit the signal(s) periodically, at the scheduled interval(s), at the time(s), at one or more other scheduled times, based on one or more triggers (e.g., based on one or more user input of other types, based on one or more occurrences of one or more operations of other types performed by the pupillary data analysis system 220, etc., or any combination thereof.

In various cases, transmitting of the signal(s) utilized to control and/or cause light emission by the computing device (s) 114 and/or the camera(s) 116 can be based on one or more signals (e.g., one or more requests) received from the computing device(s) 114 and/or the camera(s) 116. In some examples, the signal(s) may be received from the computing device(s) 114 and/or the camera(s) 116 based on the computing device(s) 114 and/or the camera(s) 116 transmitting the signal(s) (e.g., request(s)) periodically, at the one or more scheduled intervals, at one or more times, at one or more other scheduled times, based on one or more triggers (e.g., based on one or more user input of other types, based on one or more occurrences of one or more operations of other types performed by the computing device(s) 114 and/or the camera(s) 116, etc., or any combination thereof. In some examples, at least one of the signal(s) of any type being received from the computing device(s) 114 and/or the camera(s) 116 may be based on one or more selections received via user input to the computing device(s) 114 and/or the camera(s) 116.

In various examples, at least one of the selection(s) received by the computing device(s) 114, the camera(s) 116, and/or the pupillary data analysis system 220 can be utilized to identify (e.g., determine, generate, select, modify, etc., or any combination thereof) the light type data 204, the light characteristics data 206, the light level data 208, the light wavelength data 210, the light category data 212, or any combination thereof. Alternatively or additionally, identifying (e.g., determining, generating, selecting, modifying, etc., or any combination thereof) of the light type data 204, the light characteristics data 206, the light level data 208, the light wavelength data 210, the light category data 212, or any combination thereof can be based on one or more operations performed by the computing device(s) 114, the camera(s) 116, and/or the pupillary data analysis system 220.

For example, identifying (e.g., determining, generating, selecting, modifying, etc., or any combination thereof) of, and/or triggering of identification of, the light type data 204, the light characteristics data 206, the light level data 208, the light wavelength data 210, the light category data 212, or any combination thereof can be automated (e.g., performed based on execution of software, applications, etc.). In some instances, identifying (e.g., determining, generating, selecting, modifying, etc., or any combination thereof) of, and/or triggering of identification of, the light type data 204, the light characteristics data 206, the light level data 208, the light wavelength data 210, the light category data 212, or any combination thereof can be based on one or more modifications of capabilities, equipment, programming, and/or any other aspects of the computing device(s) 114, the camera(s) 116, and/or the pupillary data analysis system 220.

In some cases, the identifying (e.g., determining, generating, selecting, modifying, etc., or any combination thereof) of, and/or triggering of identification of, the light type data 204 can be based on various types of data. For example, the executable instructions to control light 228 can be performed based on the device related data 226. The device related data 226 can be utilized to identify one or more capabilities (e.g., a capability of any portion of a computing device 114 and/or a camera 116, such as software, hardware, etc., for collection of the sensor data 216 by a computing device 114 and/or a camera 116, the capability being enabled, available, etc.), one or more opportunities (e.g., an opportunity to collect sensor data based on detection of a user, and/or one or more pupils, being positioned and/or within range of a computing device 114 and/or a camera 116), and/or one or more other circumstances identified via the device related data 226.

In various implementations, the executable instructions to analyze sensor data 230 can be utilized to identify (e.g., determine, generate, select, modify, etc., or any combination thereof) the sensor data 216. For example, the identifying (e.g., determining, generating, selecting, modifying, etc., or any combination thereof) can be performed based on the device related data 214 being received from the computing device(s) 114 and/or the camera(s) 116, the light being emitted by the computing device(s) 114 and/or the camera(s) 116, the sensor data 216 being received from the computing device(s) 114 and/or the camera(s) 116, or any combination thereof.

In some examples, the executable instructions to analyze sensor data 230 being executed can include performance of one or more operations of the pupil related characteristics management system 102. For instance, the executable instructions to analyze sensor data 230 being executed can include performance of the pupil related data management component(s) 108, as discussed above with reference to FIG. 1. The executable instructions to analyze sensor data 230 can be executed to identify the pupillary data 218, which can include pupillary activity curve data (e.g., the pupillary activity curve(s)), such as the pupil response curve information (e.g., the pupil response curve(s)) (e.g., the pupillary light reflex (PLR) curve information (e.g., the PLR curve (s)).

In various implementations, the executable instructions to analyze pupillary data 232 can be utilized to analyze the pupillary data 218 (e.g., the pupillary activity curve data, including the pupillary activity curve(s), such as the pupil response curve information, including the pupil response curve(s)). In some examples, the executable instructions to analyze pupillary data 232 being executed can include performing one or more operations associated with the pupil response curve data management component(s) 110 and/or the ML model component(s) 112, as discussed above with reference to FIG. 1.

In various implementations, the system(s) 200 can include a pupil activity information management system 234. In some examples, the pupil activity information management system 234 can include pupil activity information 236, classification information 238, physiological condition information 240, and/or action information 242. In various cases, one or more types of any information (e.g., the pupil activity information 236, the classification information 238, the physiological condition information 240, and/or the action information 242) managed by the pupil activity information management system 234 can be identified (e.g., determined, generated, selected, modified, etc., or any combination thereof) based on executing of the executable instructions to analyze device related data 226, the executable instructions to control light 228, the executable instructions to analyze sensor data 230, and/or the executable instructions to analyze pupillary data 232.

Although the pupil activity information management system 234 can be separate from the pupillary data analysis system 220, as discussed above in the current disclosure, it is not limited as such. In some examples, the pupillary data analysis system 220 and the pupil activity information management system 234 can be combined and/or integrated together in various ways. In those or other examples, a portion (e.g., a partial portion or an entire portion) of the pupil activity information management system 234 can include any portion (e.g., a partial portion or an entire portion) of the pupillary data analysis system 220. In those or other examples, a portion (e.g., a partial portion or an entire portion) of the pupillary data analysis system 220 includes any portion (e.g., a partial portion or an entire portion) of the pupil activity information management system 234.

In some cases, the pupil activity information 236 can include one or more of various types of pupil activity related information, which can be identified based on analysis (e.g., analysis utilizing the ML model(s), as discussed above with reference to FIG. 1) of the pupillary data 218. For example, the pupil activity information 236 can include information (e.g., the pattern(s), the characteristic(s), as discussed above with reference to FIG. 1) utilized to identify physiological condition information (e.g., one or more physiological condition identifiers, principal component analysis (PCA) data indicating one or more PCA features with which the corresponding physiological condition identifiers are associated, or any combination thereof), which can include one or more physiological conditions.

In various examples, the classification information 238 can include one or more classifications (e.g., the classification(s), as discussed above with reference to FIG. 1) associated with the pupillary data 218. For instance, the classification(s) can be identified by analyzing (e.g., analyzing, via the ML model(s)) the pupil response curve(s) to identify the classification(s) associated with the corresponding pupil response curve(s).

In various examples, the physiological condition information 240 can include one or more physiological conditions (e.g., the physiological condition(s), as discussed above with reference to FIG. 1) based on the pupil activity information 236, the classification information 238, etc., or any combination thereof. For instance, the physiological condition(s) can be identified by analyzing (e.g., analyzing, via the ML model(s)) the pupil response curve information, the pupil activity information, and/or the classification information.

In various examples, the action information 242 can be utilized to perform one or more actions based on the pupil activity information 236, the classification information 238, the physiological condition information 240 etc., or any combination thereof. For example, the action(s) (e.g., the action(s), as discussed above with reference to FIG. 1) can be utilized to cause presentation of information (e.g., the pupil activity information 236, the classification information 238, the physiological condition information 240, etc.) by the computing device(s) 114 and/or the camera(s) 116, the pupil activity information management system 234, one or more other devices, or any combination thereof. In various cases, the action(s) can be utilized to transmit one or more signals that include information (e.g., the pupil activity information 236, the classification information 238, the physiological condition information 240, etc.) to the computing device(s) 114 and/or the camera(s) 116.

In some cases, the action information 242 can be utilized to perform the action(s), which can include presenting information (e.g., the pupil activity information 236, the classification information 238, the physiological condition information 240, etc.) by the pupil activity information management system 234. In various cases, the action information 242 can be utilized to perform the action(s), which can include transmitting one or more signals that include information (e.g., the pupil activity information 236, the classification information 238, the physiological condition information 240, etc.) to the computing device(s) 114 and/or the camera(s) 116

In some implementations, utilizing the action information 242 to perform the action(s) can be automated. For example, at least one of the action(s) can be periodically performed by the pupillary data analysis system 220. In some examples, at least one of the action(s) can be performed by the pupil activity information management system 234 at one or more scheduled intervals. In some examples, at least one of the action(s) can be performed by the pupil activity information management system 234 at one or more times (e.g., one or more moments in time).

Any of the various ways of performing the action(s) by the pupil activity information management system 234 utilizing the action information 242 may be based on, for instance, user input. In some examples, one or more selections received via user input to the pupil activity information management system 234 can be identified. In those or other examples, at least one of the selection(s) can include data utilized to perform, and/or to triggering performance of, the action(s) periodically, at the scheduled interval(s), at the time(s), at one or more other scheduled times. For example, the action(s) can be performed by the pupil activity information management system 234 based on one or more triggers (e.g., based on one or more user input of other types, based on one or more occurrences of one or more operations of other types performed by the pupil activity information management system 234, etc., or any combination thereof.

In various cases, the action(s) can include one or more actions performed, by the computing device(s) 114 and/or the camera(s) 116, based on the pupil activity information management system 234 transmitting one or more signals to the computing device(s) 114 and/or the camera(s) 116. The signal can be transmitted by the pupil activity information management system 234 based on the pupil activity information 236, the classification information 238, the physiological condition information 240, etc., being identified (e.g., determined, generated, selected, modified, etc., or any combination thereof).

While the executable instructions to analyze device related data 226, the executable instructions to control light 228, the executable instructions to analyze sensor data 230, and/or the executable instructions to analyze pupillary data 232 can be executed by the pupillary data analysis system 220, and/or the pupil activity information 236, the classification information 238, the physiological condition information 240, and/or the action information 242 can be managed by the pupil activity information management system 234, as discussed above in the current disclosure, it is not limited as such. In some examples, any of the executable instructions to analyze device related data 226, the executable instructions to control light 228, the executable instructions to analyze sensor data 230, and/or the executable instructions to analyze pupillary data 232 can be executed by the computing device(s) 114 and/or the camera (s) 116, alternatively or additionally to the pupillary data analysis system 220. In those or other examples, any of the pupil activity information 236, the classification information 238, the physiological condition information 240, and/or the action information 242 can be managed by the computing device(s) 114 and/or the camera(s) 116, alternatively or additionally to the pupil activity information management system 234.

In some cases, the at least one of the selection(s) received by the computing device(s) 114, the camera(s) 116, and/or the pupil activity information management system 234 can be utilized to identify (e.g., determine, generate, select, modify, etc., or any combination thereof), and/or to triggering identifying of, one or more of the action(s) to be performed. Alternatively or additionally, the action(s) can be performed by the computing device(s) 114 and/or the camera(s) 116 based on (e.g., triggered by) any of one or more other operations performed by of the computing device(s) 114, the camera(s) 116, and/or the pupil activity information management system 234.

For example, identifying (e.g., determining, generating, selecting, modifying, etc., or any combination thereof) of the action(s) to be performed by the computing device(s) 114 and/or the camera(s) 116 can be automated by the computing device(s) 114 and/or the camera(s) 116 (e.g., performed based on execution of software, applications, etc., of the computing device(s) 114 and/or the camera(s) 116). In some instances, identifying (e.g., determining, generating, selecting, modifying, etc., or any combination thereof) of the action(s) to be performed by the computing device(s) 114 and/or the camera(s) 116 can be based on (e.g., triggered by) one or more modifications of capabilities, equipment, programming, and/or any other aspects of the computing device (s) 114 and/or the camera(s) 116.

Although the pupillary data analysis system 220 and the pupil activity information management system 234 can be included in the pupil related characteristics management system 102, as discussed above in the current disclosure, it is not limited as such. In some examples, one or more components of the pupillary data analysis system 220 and/or one or more components of the pupil activity information management system 234 can be included in at least one of the computing device(s) 114 and/or at least one of the camera(s) 116. For example, any number of the one or more components of the pupillary data analysis system 220 and/or any number of the one or more components of the pupil activity information management system 234 can be provided by any number of the at least one of the computing device(s) 114 and/or at least one of the camera(s) 116, separately. Alternatively, any number of the one or more components of the pupillary data analysis system 220 and/or any number of the one or more components of the pupil activity information management system 234 can be provided by distributed processing via a combination of devices (e.g., a combination of any number of the computing device(s) 114 and/or any number of the camera(s) 116).

Figure 3:
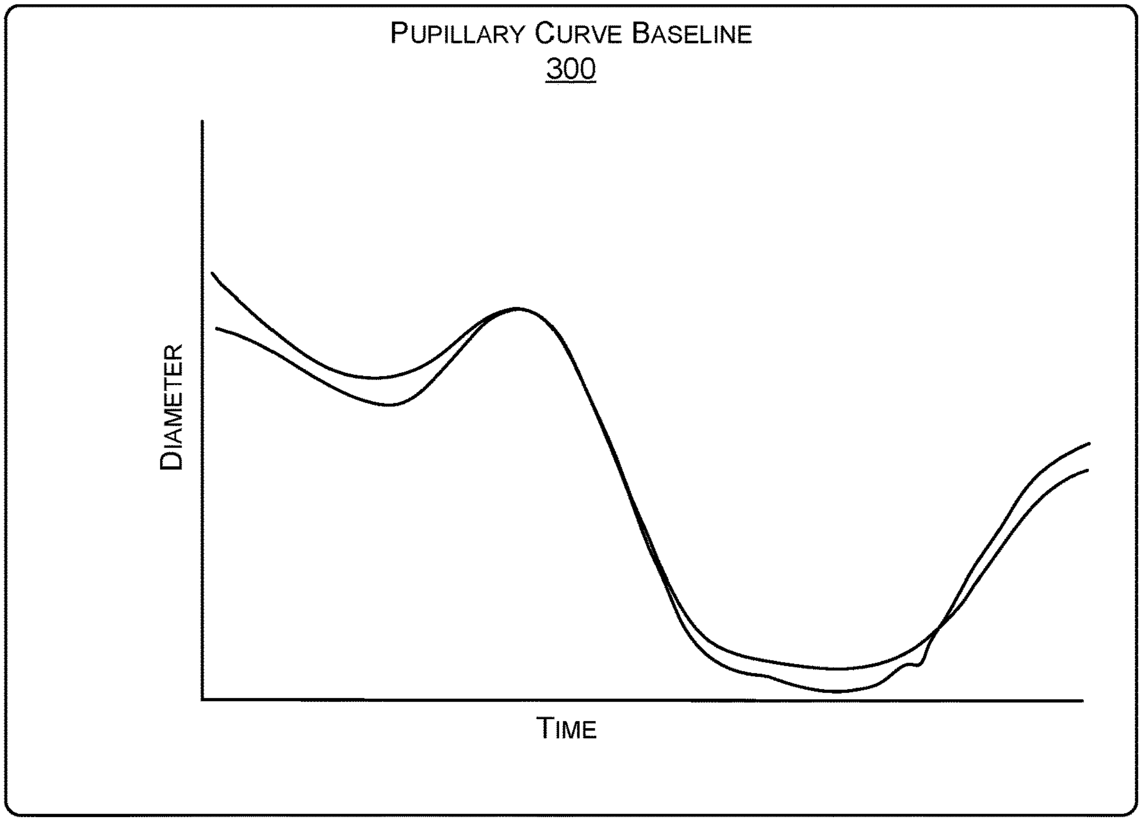
FIG. 3 depicts an example pupillary curve baseline and an example pupillary curve.
Figure 3:
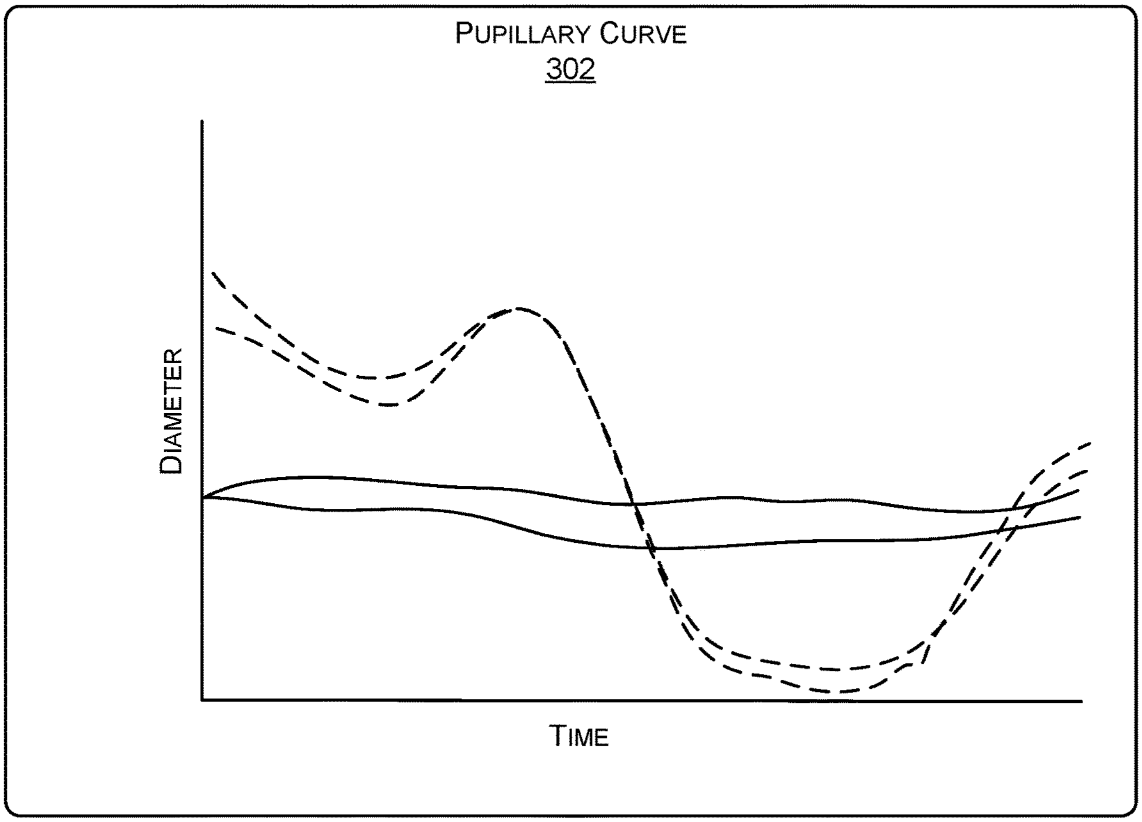

FIG. 3 depicts an example pupillary curve baseline 300 and an example pupillary curve 302. For example, the pupillary curve baseline 300 can be utilized as a representative pupillary curve that is not associated with any physiological condition.

In various examples, the pupillary curve 302 (e.g., two lines representing two curves for two pupils, respectively) may be associated with a user. The pupillary curve baseline 300 (e.g., two lines representing two curves for two pupils, respectively may be representative of one or more various pupillary curves (e.g., one or more pupillary light reflex (PLR) curves) associated with one or more various users (e.g., one or more users for which one or more pupillary curves were previously analyzed, and, possibly, utilized for training of one or more machine learning (ML) models (e.g., the ML model(s) utilized by the ML model component(s) 112, as discussed above with reference to FIG. 1)).

In some examples, various types of data (e.g., the light type data 204, the light characteristics data 206, the light level data 208, the light wavelength data 210, the light category data 212, or any combination thereof, as discussed above with reference to FIG. 2), can be identified, and utilized to identify other types of data (e.g., the sensor data 216, the pupillary data 218, etc., as discussed above with reference to FIG. 2) associated with pupil response curve generation (e.g., pupillary light reflex (PLR) curve generate). In those or other examples, the pupillary data 218 can be utilized to identify various type of information (e.g., pupil activity information 236, classification information 238, physiological condition information 240, and/or action information 242, as discussed above with reference to FIG. 2).

In some cases, the pupillary data 218 can include the pupillary curve baseline 300 and the pupillary curve 302. In various examples, the pupillary data 218 can include a pupillary curve (e.g., a pupil response curve) utilized as the pupillary curve baseline 300, being identified as a training pupillary curve for the ML models.

In some examples, the physiological condition information 240 can include information associated with one or more physiological conditions (e.g., a coma, a vegetative state, one or more other physiological conditions of other types, or any combination thereof). The physiological condition can be identified by an analysis system (e.g., the pupillary data analysis system 220).

In some cases, analysis is performed utilizing the ML model(s), based on the comparison(s) between the pupillary curve 302 (e.g., the pupillary curve 302, being a current pupillary activity curve (e.g., a current pupil response activity curve)) and one or more other pupillary activity curves (e.g., the training pupillary activity curve(s). The comparison(s) can be performed, via the ML model(s), by the ML model(s) being utilized to perform support vector machine (SVM) analysis of the current pupillary activity curve. The SVM analysis can be performed based on the pupillary activity curves in one or more databases (e.g., the library database(s), as discussed in further detail below).

In various examples, analysis of the pupillary curve 302 can be utilized to identify the pupillary curve 302 as being associated with the physiological condition(s), based on one or more comparison(s) performed utilizing the ML model(s). In some cases, the comparison(s) can be performed utilizing one or more curve classification algorithms. For example, the curve classification algorithm(s) can be utilized by the ML model(s) to match the pupillary curve 302 with another curve (e.g., a curve with the physiological condition(s)) (e.g., another pupil response curve) to identify the physiological condition(s) based on the pupillary curve 302 being associated with the physiological condition(s).

In some examples, one or more characteristics associated with a user with which the pupillary curve 302 is associated can be utilized to match the pupillary curve 302 with one or more other curves. For example, the characteristic(s) (e.g., at least one of a gender, an age, or an eye color, one or more other characteristic(s), or any combination thereof) can be utilized to match the pupillary curve 302 with the other curve(s). At least one of the characteristic(s) of the pupillary curve 302 being the same as, or similar to, at least one of the characteristic(s) of the other curve(s) can be characteristic (s).

Any of the other curve(s) including one or more similarities (e.g., similar "change(s)" in the curve(s)) to the pupillary curve 302 can be further utilized to match the pupillary curve 302 with the other pupillary curve. The other pupillary curve being associated with at least one physiological condition can be utilized to identify the at least one physiological condition as being associated with the pupillary curve 302.

In some examples, the ML model(s) can utilize the pupil response curve 302 being matched with the other pupillary curve to output, by the ML model, one or more predictive performance measurements associated with the pupillary curve 302. For instance, the predictive performance measurement may indicate a probability of a future likelihood of the user (e.g., an individual) experiencing the at least one physiological condition (e.g., at least one of a coma or a vegetative state).

In some examples, performing, by the ML model(s), the comparison(s) between a current pupillary activity curve (e.g., the pupillary curve 302) and one or more pupillary activity curves (e.g., one or more training pupillary activity curves) can be based on various characteristics associated with various individuals. For instance, the comparison(s) can include matching at least one characteristic of the user (e.g., an individual) with at least one corresponding characteristic of individual ones of a first subset of the individuals (e.g., a subset of one or more training individuals) associated with the pupillary activity curve(s) (e.g., the training pupillary activity curve(s)). In some cases, the at least one characteristic can include at least one of a gender, an age, a clinical datapoint, or an eye color.

In some cases, the comparison(s) can be performed between the current pupillary activity curve and a second subset of the pupillary activity curves associated with the first subset of the individuals. The second subset can be identified based on one or more updated characteristics (e.g., at least one of an updated gender, an updated age, an updated eye color, or one or more other newly identified characteristics), based on a number of similarities (e.g., matching portions of the curves) of the current pupillary activity curve to individual pupillary activity curves of the second subset being more prevalent (e.g., higher) a number of similarities (e.g., matching portions of the curves) of the current pupillary activity curve to individual pupillary activity curves of the first subset. The first subset can be changed to the second subset.

In some examples, one or more matches between one or more portions of the current pupillary activity curve and one or more corresponding portions of individual pupillary activity curves of the second subset can be utilized to identify physical conditions associated with the individual pupillary activity curves of the second subset. The physical conditions associated with the individual pupillary activity curves of the second subset can be identified as being associated with the current pupillary activity curve based on the match(es).

Although the pupillary data 218 can include the pupillary curve(s), as discussed in the current disclosure, it is not limited as such. In some examples, a portion (e.g., a partial portion or an entire portion) of the pupillary data 218 (e.g., a portion of the training pupillary curve(s)) can be stored in the database(s) (e.g., one or more pupillary curve databases) (e.g., one or more pupil response curve databases) (or "relational database(s)") (or "library database(s)") (e.g., a group of databases, which can include database files that include an array of numbers, a string of numbers, etc., or any combination thereof). In various cases, the pupillary curve database(s) can be updated on an ongoing basis as new pupillary curve(s) are analyze utilizing the ML model(s). The database(s) can be stored, for example, by a data management system (e.g., the device, light, and pupillary data management system 202, as discussed above with reference to FIG. 2).

For instance, with examples in which the database(s) store the pupillary data 218, a database can include one or more columns. Individual ones of the columns can include a timestamp associated with values along a pupillary curve in the database. In some cases, individual ones of one or more entries can be included in the database for various periods of time (e.g., a value, such as a characteristic (e.g., diameter) of a pupil, can be captured 30 times/second, 60 times/second, 120 times/second, etc.). The database can capture one or more other correlated events that occur during a time and that are detectable by a camera (e.g., any of the camera(s) 116) and/or one or more sensors (e.g., the sensor(s) as discussed above with reference to FIG. 1, such as one or more sensors of a corresponding computing device 114, one or more sensors of a corresponding camera 116) that are utilized to create a data frame.

In various examples, the characteristic(s) being analyzed to identify data in the pupillary data 218 can include pupillary distance. For instance, the pupillary distance analyzed based on the pupillary data 218 can include interpupillary distances (IPDs) (or "binocular PDs"), including a distance between centers of two pupils.

In various implementations, analyze of the pupillary curve 302 can be performed based on one or more queries to the database(s). For example, one or more signals (e.g., the signal(s), as discussed above with reference to FIG. 2), can include one or more query signals (or "query(ies)") to the database(s). The query signal(s) can be utilized to identify (e.g., determine, receive, obtain, retrieve, etc. or any combination thereof) one or more signals including data based on the query(ies). For example, the pupillary data analysis system 220 can query the database(s) to retrieve data (e.g., one or more portions of the pupillary data 218) utilized by the ML model(s) to analyze the pupillary curve 302.

In various cases, the pupillary data 218 can be managed by storing the pupillary data 218 in the database(s) as one or more spreadsheets (e.g., one or more spreadsheet program formatted files). For some examples, the pupillary data 218 can be stored in the spreadsheet(s), in the database(s). Alternatively or additionally, the pupillary data 218 can be stored separately from the database(s).

In some examples, the pupillary data 218 can be stored in the spreadsheet(s) and/or the database(s) along with one or more parameters. The parameter(s) can be identified along with, and/or as part of, the pupillary data 218. The parameter(s) can include one or more timeframes, one or more timestamps, one or more diameters of each pupil, one or more measured illuminations of an environment in which the user is positioned, one or more other events that are "important" to identify in individual ones of the timeframe(s). For example, the parameter(s) can include a value indicating whether a user blinks one or more times at some point in time (e.g., 3 seconds into gathering of the pupillary data 218), or whether one or more light stimuli are activated, whether a vulva stimulus occurs, whether some other stimulus occurs, one or more timestamps associated with any of the parameter(s)/occurrence(s) and/or one or more other parameters and/or occurrences.

In some cases, the parameter(s) can be stored with the pupillary data 218. For example, the parameter(s) can be stored in the spreadsheet(s) and/or the database(s).

The ML model(s) can utilize any of the pupillary data 218 and/or one or more other types of data for analysis of the pupillary data 218. For example, the ML model(s) can identify the physiological condition(s) associated with corresponding pupillary curve(s) based on corresponding parameter(s) associated with gathering of the data in the corresponding pupil response curve(s).

In some examples, the analysis performed by the ML model(s) can be utilized to tag (e.g., generate one or more tags) associated with the pupillary curve(s). The tag(s) can be stored with the pupillary data 218. For example, the tag(s) can be stored in the spreadsheet(s) and/or the database(s). Generation of the tag(s) can be utilized to "tag" individual ones of the pupillary curve(s) with any known diagnosis and/or prognosis information. In some cases, the tag(s) can be utilized to indicate information associated with the user (e.g., injury, intoxication, deception, a mental state, fatigue, dementia, toxins, disease, a heart condition, diabetes, or one or more other information of other types).

Data associated with the tag(s), which can be generated separately from the tag(s) in a similar way, can be included in one or more portions of metadata on the curve itself along with the user related data. Any of the tag(s) associated with one or more conditions of individual ones of the users, and/or condition data (e.g., data identifying a condition, such as intoxication), etc., can be stored with the pupillary data 218. For example, the tag(s), and/or the condition data, stored in the spreadsheet(s) and/or the database(s) along with the pupillary curve(s). Any of the information stored in the spreadsheet(s) and/or the database(s) can be linked via the metadata, and/or identified via links, to correspond pupillary curve(s)).

In various cases, performing ongoing updates of the pupillary curve database(s) can include maintaining the library data in the library database. In some examples, maintaining the library data can be performed via ongoing analysis of additional sensor data associated with one or more additional individuals. In those or other examples, the maintaining of the library data can be performed via ongoing collection of one or more additional pupillary activity curves based on the additional sensor data. In those or other examples, the maintaining of the library data can be performed via ongoing generation of one or more additional classification models based on the additional pupillary activity curve(s).

In those or other examples, the maintaining of the library data can be performed via updating of the baselines as updated baselines based on the additional pupillary activity curve(s). In those or other examples, the maintaining of the library data can be performed via updating of the library data based on the additional pupillary activity curve(s), the additional classification model(s), and the updated baseline (s), the additional classification model(s) being utilized to relatively increase a level of accuracy of ongoing identification of additional physiological condition(s) associated with the additional pupillary activity curve(s).

In some examples, individual ones of the pupillary curve (s) can represent information (e.g., at least one curve characteristic of the curve characteristic(s)) associated with at least one pupil. In those or other examples, individual ones of the pupillary curve(s) can represent information associated with corresponding pairs of pupils. In those or other examples, the pupillary curve can represent at least one change of at least one pupil in a pair of pupils with which the sensor data is associated (e.g., at least one change of diameter of at least one pupil in the pair of pupils, at least one change of size of at least one pupil in the pair of pupils, or any combination thereof).

In some cases, individual ones of the pupillary curve(s) can represent at least one change of both pupils in a pair of pupils with which the sensor data is associated. For instance, with examples in which a pupillary curve represents data associated with a pair of pupils, the pupillary curve can represent at least one change of both pupils in the pair of pupils with which the sensor data is associated (e.g., at least one change of diameter of both pupils in the pair of pupils, at least one change of size of both pupils in the pair of pupils, or any combination thereof). In some cases, the at least one change can include "identical" changes, "matching" changes, "similar" changes, changes different from one another be less than a threshold change, changes withing a threshold margin from one another, etc., or any combination thereof, associated with both pupils.

In some examples, at least one change identified via a pupillary curve can include a plurality of changes of both pupils of the pair of pupils. The plurality of changes of various types can include a series of changes, a group of periodic changes, "seemingly random" changes, aperiodic changes, "significant" changes (e.g., any change of an amount greater than a threshold pupillary curve change amount), "insignificant" changes (e.g., any change of an amount lower than a threshold pupillary curve change amount), sporadic changes, any other types of changes, or any combination thereof. The various types of changes can be utilized, as a pupillary curve and/or a group of pupillary curve changes, to identify the pair of pupils (e.g., the user) with which the pupillary curve is associated.

In some examples, the at least one change identified via a pupillary curve can include an average change for both pupils in the pair of pupils with which the sensor data is associated (e.g., an average change of diameter for individual ones of any number of changes of pupil diameter of both pupils in the pair of pupils, an average change of size for individual ones of any number of changes of pupil size of both pupils in the pair of pupils, or any combination thereof).

In those or other examples, the at least one change identified via a pupillary curve can include a largest change for both pupils in the pair of pupils with which the sensor data is associated (e.g., a largest change of diameter for individual ones of any number of changes of pupil diameter of both pupils in the pair of pupils, a largest change of size for individual ones of any number of changes of pupil size of both pupils in the pair of pupils, or any combination thereof). In those or other examples, the at least one change identified via a pupillary curve can include a smallest change for both pupils in the pair of pupils with which the sensor data is associated (e.g., a smallest change of diameter for individual ones of any number of changes of pupil diameter of both pupils in the pair of pupils, a smallest change of size for individual ones of any number of changes of pupil size of both pupils in the pair of pupils, or any combination thereof).

In alternative examples, individual ones of a pair of the pupillary curve(s) can represent information associated with corresponding pupils in corresponding pairs of pupils. For instance, with examples in which a pupillary curve represents data associated with a pair of pupils, the pupillary curve can represent at least one change of a single pupil in the pair of pupils with which the sensor data is associated (e.g., at least one change of diameter of a single pupil in the pair of pupils, at least one change of size of a single pupil in the pair of pupils, or any combination thereof), in a similar way as discussed above for the pupillary curve being utilized to identify the change(s) in both pupils.

Although the pupillary curve(s) representing data associated with the corresponding pair(s) of pupils can be utilized to identify various changes in both pupils in the pair of pupils or in a single pupil in the pair of pupils, as discussed above in the current disclosure, it is not limited as such. In those or other examples, a pupillary activity curve (e.g., a pupillary curve associated with a diameter, a size, a PLR, any other pupil characteristics, or any combination thereof, associated with a pupil or a pair of pupils, the pupillary curve being identified based on internal and/or external stimuli associated with "non-specialized" non-flashing light and/or "specialized" flashing light, respectively) (e.g., a pupil response curve) can represent a change of a pupil based on an amount of the change being different from another amount of another change of another pupil, the other change being represented by the pupillary activity curve (e.g., the pupillary curve) (e.g., the pupil response curve) and/or another pupillary activity curve (e.g., another pupil response curve).

Although the pupillary curve(s) representing data associated with the corresponding pair(s) of pupils can be utilized to identify various changes both pupils in the pair(s) of pupils, as discussed above in the current disclosure, it is not limited as such. In some examples, individual ones of at least one pupillary activity curve (e.g., at least one pupillary curve) can represent a change of a pupil in a pair of pupils based on another pupil of the pair of pupils not changing. In those or other examples, individual ones of the pupillary curve(s) represent a change of a pupil based on another pupil not changing can be utilized in a similar way as for the pupillary curve(s) utilized to identify various changes of at least one pupil, to implement any of the techniques discussed herein.

Although the pupillary curve(s) may represent data associated with various types of changes in at least one pupil, as discussed above in the current disclosure, it is not limited as such. In some examples, the pupillary curve(s) can be utilized to identify any number of changes of a pupil in a pair of pupils, both pupils in the pair of pupils, etc., or any combination thereof, at any number of corresponding times. The pupillary curve(s) can be utilized to identify occurrences of patterns, absences of occurrences of patterns, etc., or any combination thereof, which may be associated with the changes of any number at the corresponding times.

Although a single pupillary activity curve can represent data associated with both pupils of corresponding pair(s) of pupils, as discussed above in the current disclosure, it is not limited as such. In various implementations, a pair of pupillary activity curves (e.g., a pair of pupil response curves) can include corresponding portions of time series curve data (e.g., a pair of portions of time series curve data) for a pair of corresponding pupils of a user. In such an example, the pair of curves associated with a pair of pupils can be utilized in a similar way as any single curve associated with the pair of pupils, to implement any of the techniques discussed herein. For instance, with such examples in which a pair of pupillary curves includes corresponding portions of the time series curve data, the pair of pupillary curves can be utilized to identify one or more changes of one or both of the pupils in the pair of pupils.

Although the pupillary activity curve(s) (e.g., pupil response curve(s)) can represent data for both pupils, individual ones of the pupillary curve(s) can represent data associated with a single pupil with which the sensor data is associated, omitting data associated with another pupil. For example, a pupillary curve can be utilized to identify at least one change for the single pupil in a similar way as discussed above for the pupillary curve(s) associated with a pair of pupils. In such an example, the pupillary curve, which can represent at least one change for the single pupil, can be utilized in a similar way as any single curve associated with the pair of pupils, to implement any of the techniques discussed herein.

As a hypothetical example, a user can operate a computing device, such as a cellular phone, which can record video data while it is being used by the user. The video data can include data associated with pupils of the user. By recording data about both pupils at the same time, analysis of potential physiological conditions of the user can be optimized. The video data can be "passively" captured while no light related to the capturing of the video data is emitted. However, a flash of light can also be emitted while the video data is being captured.

In the hypothetical example, analysis of the video data can be performed by the cellular phone or by a centralized server or group of servers. The analysis can include identify at least one curve represented by the data. For example, the at least one curve can represent data associated with characteristics of the pupils, such as at least one diameter of one or both pupils. Various changes in the at least one diameter may be represented by the at least one curve. In some cases, a single curve can be utilized to capture data representing both pupils.

In the hypothetical example, analysis can include comparing the curve to other curves, such as previously stored curves. The other curves can be identified in similar ways as for the curve being currently analyzed. The other curves may also include training curves, used to train an ML model that is being utilized to perform the analysis. The training of the ML model may include identifying classifications for the previous curves. The classifications can be utilized to associate the previous curves with user characteristics (e.g., eye color, age, etc.), and/or with states of the user (e.g., injury, intoxication, deception, a mental state, fatigue, dementia, toxins, disease, a heart condition, diabetes, or one or more other information of other types), and/or with one or more physiological conditions (e.g., a coma, a vegetative state, diseases, medical conditions, any other physiological conditions, etc., or any combination thereof). For example, one or more diseases, with which the previous curves are associated, include diabetes, heart failure, other general medical conditions that can be examined via the pupil(s), or any combination thereof.

In the hypothetical example, classification models representing mathematically generated classifications as the classifications, can be utilized as part of the ML model and/or can be utilized along with the ML model. The classifications can be identified via classification tags and can be stored with the classification tags as a portion of library data in library databases. The library data can include any other relevant data such as the curves. The curves can also include pupillary activity curves, such as pupil response curves.

In the hypothetical example, by using the comparison, the current curve can be matched with various subsets of the previous curves. The matching can be performed based on changes and/or characteristics of the curves. The matching can be performed based on user characteristics matching, and/or user states matching. If the current user has blue eyes and intoxicated, the curve can be compared to previous curves associated with users with blue eyes and that are intoxicated. Based on the matching, physiological conditions can be identified based on other changes and/or characteristics of the curves.

In the hypothetical example, variations between the current curve and baselines can be utilized to identify any physiological conditions associated with the current curve. The baselines can be identified via consolidation of pupillary activity data, including the pupillary activity curves. A baseline can represent a known physiological curve without any physiological conditions (e.g., a known physiological curve without any physiological conditions can be identified as a "baseline"). The baselines can be identified via, and/or linked to, baseline tags. The baselines can be stored with the baseline tags in the library data in the library databases.

In the hypothetical example, if the current curve for the user matches the other curves for users with blue eyes and that are intoxicated and that do not have any physiological conditions, then the result can be identified as "normal." If the current curve for the user matches the other curves for users with blue eyes and that are intoxicated and that have experienced a coma, then the curve can be flagged. By flagging the curve with a value and/or identifier representing the coma, the value and/or the identifier can be transmitted along with the curve to a physician of the user, the user (in some cases), or any other designated device.

In the hypothetical example, any types of previous curves associated with any similar and/or different characteristics can be utilized for the comparison. The comparison can be performed in real time to provide feedback to the user.

In the hypothetical example, the comparison can be utilized to identify other information about the user such as the user characteristics and/or the user state. The comparison can be utilized to transmit data to a device of an officer to indicate that the user has blue eyes, notwithstanding the user appearing to have brown eyes due to the user wearing contacts. The comparison can be utilized to transmit data to a device of an officer to indicate that the user is intoxicated. Any details based on similarities and/or differences between the current curve and previous curves can be utilized to identify data and to present results and/or transmit results.

In the hypothetical example, the ML model can be trained in real-time and/or on an ongoing basis. As information is collected about users, results data such as flags can be sent to users (e.g., operators) based on results of comparisons. The results data can be utilized by the operators to train and/to improve the ML models.

Figure 4:
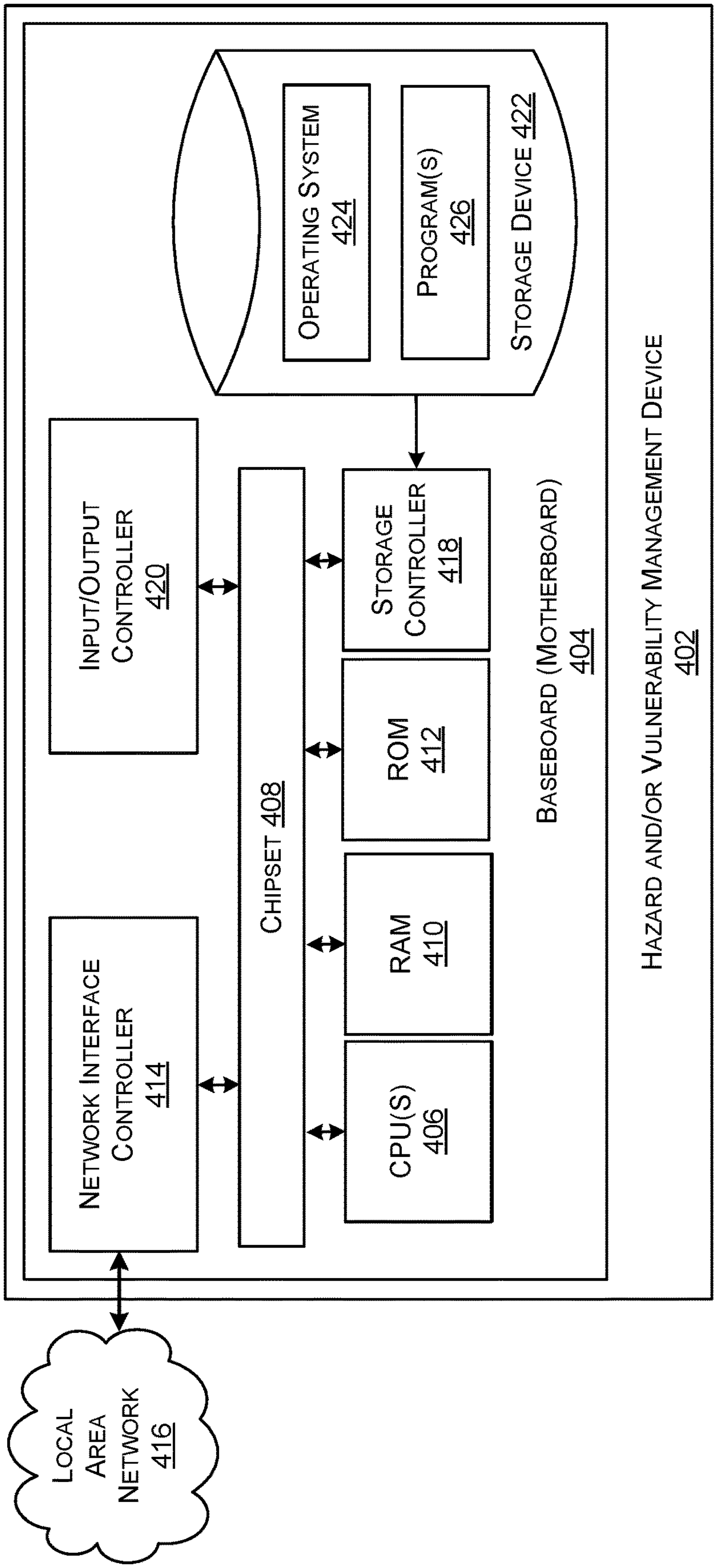
FIG. 4 depicts an example computer architecture for a computing device (e.g., a computing device utilized as part of a pupil related characteristics management system) capable of executing program components for implementing the functionality described above.

FIG. 4 depicts an example computer architecture for a computing device (e.g., a computing device utilized as part of a pupil related characteristics management system 102) capable of executing program components for implementing the functionality described above. The computer architecture shown in FIG. 4 illustrates a conventional server computer, workstation, desktop computer, laptop, tablet, network appliance, e-reader, smartphone, or other computing device, and can be utilized to execute any of the software components presented herein. The computing device 402 may, in some examples, correspond to a physical server and may comprise networked devices such as servers, switches, routers, hubs, bridges, gateways, modems, repeaters, access points, etc. In some examples, the computing device 402 can be utilized to implement any of one or more devices in individual ones of the pupil related characteristics management system 102, device, light, and pupillary data management system 202, the pupillary data analysis system 220, and the pupil activity information management system 234.

The computing device 402 includes a baseboard 404, or "motherboard," which is a printed circuit board to which a multitude of components or devices can be connected by way of a system bus or other electrical communication paths. In one illustrative configuration, one or more central processing units ("CPUs") 406 (e.g., the processor(s) 104, as discussed above with reference to FIG. 1) operate in conjunction with a chipset 408. The CPUs 406 can be standard programmable processors that perform arithmetic and logical operations necessary for the operation of the computing device 402.

The CPUs 406 perform operations by transitioning from one discrete, physical state to the next through the manipulation of switching elements that differentiate between and change these states. Switching elements generally include electronic circuits that maintain one of two binary states, such as flip-flops, and electronic circuits that provide an output state based on the logical combination of the states of one or more other switching elements, such as logic gates. These basic switching elements can be combined to create more complex logic circuits, including registers, adders-subtractors, arithmetic logic units, floating-point units, and the like.

The chipset 408 provides an interface between the CPUs 406 and the remainder of the components and devices on the baseboard 404. The chipset 408 can provide an interface to a RAM 410, used as the main memory in the computing device 402. The chipset 408 can further provide an interface to a computer-readable storage medium such as a read-only memory ("ROM") 412 or non-volatile RAM ("NVRAM") for storing basic routines that help to startup the computing device 402 and to transfer information between the various components and devices. The ROM 412 or NVRAM can also store other software components necessary for the operation of the computing device 402 in accordance with the configurations described herein.

The computing device 402 can operate in a networked environment using logical connections to remote computing devices and computer systems through a network, such as one or more networks 416. The chipset 408 can include functionality for providing network connectivity through a network interface controller (NIC) 414, such as a gigabit ethernet adapter. The NIC 414 is capable of connecting the computing device 402 to other computing devices over the network(s) 416. In some examples, individual ones of one or more networks can be implemented according to the network(s) 416, and utilized to implement the network(s) 416. It should be appreciated that multiple NICs 414 can be present in the computing device 402, connecting the computer to other types of networks and remote computer systems.

The computing device 402 can be connected to a storage device 422 that provides non-volatile storage for the computing device 402. The storage device 422 can store one or more operating systems 424, one or more programs 426, and data, which have been described in greater detail herein. The storage device 422 can be connected to the computing device 402 through a storage controller 418 connected to the chipset 408. The storage device 422 can consist of one or more physical storage units. The storage controller 418 can interface with the physical storage units through a serial attached SCSI ("SAS") interface, a serial advanced technology attachment ("SATA") interface, a fiber channel ("FC") interface, or other type of interface for physically connecting and transferring data between computers and physical storage units.

The computing device 402 can store data on the storage device 422 by transforming the physical state of the physical storage units to reflect the information being stored. The specific transformation of physical state can depend on various factors, in different embodiments of this description. Examples of such factors can include, but are not limited to, the technology used to implement the physical storage units, whether the storage device 422 is characterized as primary or secondary storage, and the like.

For example, the computing device 402 can store information to the storage device 422 by issuing instructions through the storage controller 418 to alter the magnetic characteristics of a particular location within a magnetic disk drive unit, the reflective or refractive characteristics of a particular location in an optical storage unit, or the electrical characteristics of a particular capacitor, transistor, or other discrete component in a solid-state storage unit. Other transformations of physical media are possible without departing from the scope and spirit of the present description, with the foregoing examples provided only to facilitate this description. The computing device 402 can further read information from the storage device 422 by detecting the physical states or characteristics of one or more particular locations within the physical storage units.

In addition to the mass storage device 422 described above, the computing device 402 can have access to other computer-readable storage media to store and retrieve information, such as program modules, data structures, or other data. It should be appreciated by those skilled in the art that computer-readable storage media is any available media that provides for the non-transitory storage of data and that can be accessed by the computing device 402. In some examples, the operations performed by the environment 100, and or any components included therein, may be supported by one or more devices similar to computing device 402. Stated otherwise, some or all of the operations performed by the pupil related characteristics management system 102, device, light, and pupillary data management system 202, the pupillary data analysis system 220, and the pupil activity information management system 234, and or any components included therein, may be performed by one or more computing device 402 operating in a cloud-based arrangement.

By way of example, and not limitation, computer-readable storage media can include volatile and non-volatile, removable and non-removable media implemented in any method or technology. Computer-readable storage media includes, but is not limited to, RAM, ROM, erasable programmable ROM ("EPROM"), electrically-erasable programmable ROM ("EEPROM"), flash memory or other solid-state memory technology, compact disc ROM ("CD-ROM"), digital versatile disc ("DVD"), high definition DVD ("HD-DVD"), BLU-RAY, or other optical storage, magnetic cassettes, magnetic tape, magnetic disk storage or other magnetic storage devices, or any other medium that can be used to store the desired information in a non-transitory fashion.

As mentioned briefly above, the storage device 422 can store an operating system 424 utilized to control the operation of the computing device 402. According to one embodiment, the operating system comprises the LINUX operating system. According to another embodiment, the operating system comprises the WINDOWS® SERVER operating system from MICROSOFT Corporation of Redmond, Washington. According to further embodiments, the operating system can comprise the UNIX operating system or one of its variants. It should be appreciated that other operating systems can also be utilized. The storage device 422 can store other system or application programs and data utilized by the computing device 402.

In one embodiment, the storage device 422 or other computer-readable storage media is encoded with computer-executable instructions which, when loaded into the computing device 402, transform the computer from a general-purpose computing system into a special-purpose computer capable of implementing the embodiments described herein. These computer-executable instructions transform the computing device 402 by specifying how the CPUs 406 transition between states, as described above. According to one embodiment, the computing device 402 has access to computer-readable storage media storing computer-executable instructions which, when executed by the computing device 402, perform the various processes described above with regard to FIGS. 1-3. The computing device 402 can also include computer-readable storage media having instructions stored thereupon for performing any of the other computer-implemented operations described herein.

The computing device 402 can also include one or more input/output controllers 420 for receiving and processing input from a number of input devices, such as a keyboard, a mouse, a touchpad, a touch screen, an electronic stylus, or other type of input device. Similarly, an input/output controller 420 can provide output to a display, such as a computer monitor, a flat-panel display, a digital projector, a printer, or other type of output device. It will be appreciated that the computing device 402 might not include all of the components shown in FIG. 4, can include other components that are not explicitly shown in FIG. 4, or might utilize an architecture completely different than that shown in FIG. 4.

As described herein, one or more computers (e.g., the pupil related characteristics management system 102, device, light, and pupillary data management system 202, the pupillary data analysis system 220, the pupil activity information management system 234, and/or one or more other computers) may comprise one or more the device(s). In various examples, computing device 402 may comprise individual ones of one or more devices being implemented as any of the devices and/or servers in any of the pupil related characteristics management system 102. The computer(s) may include one or more hardware processors (processors) configured to execute one or more stored instructions. The processor(s) may comprise one or more cores. Further, the computer(s) may include one or more network interfaces configured to provide communications between the computer(s) and other devices, such as the communications described herein as being performed by the pupil related characteristics management system 102, device, light, and pupillary data management system 202, the pupillary data analysis system 220, the pupil activity information management system 234, and/or one or more of any other devices communicatively coupled thereto (e.g., the computing device(s) 114, the camera(s) 116, etc.). The network interfaces may include devices configured to couple to personal area networks (PANs), wired and wireless local area networks (LANs), wired and wireless wide area networks (WANs), and so forth. For example, the network interfaces may include devices compatible with Ethernet, Wi-Fi™, and so forth.

The programs may comprise any type of programs or processes to perform the techniques described in this disclosure for providing hazard and/or vulnerability management utilizing natural disaster shed data. The programs may comprise any type of program that cause the computer(s) to perform techniques for communicating with other devices using any type of protocol or standard usable for determining connectivity.

Figure 5:
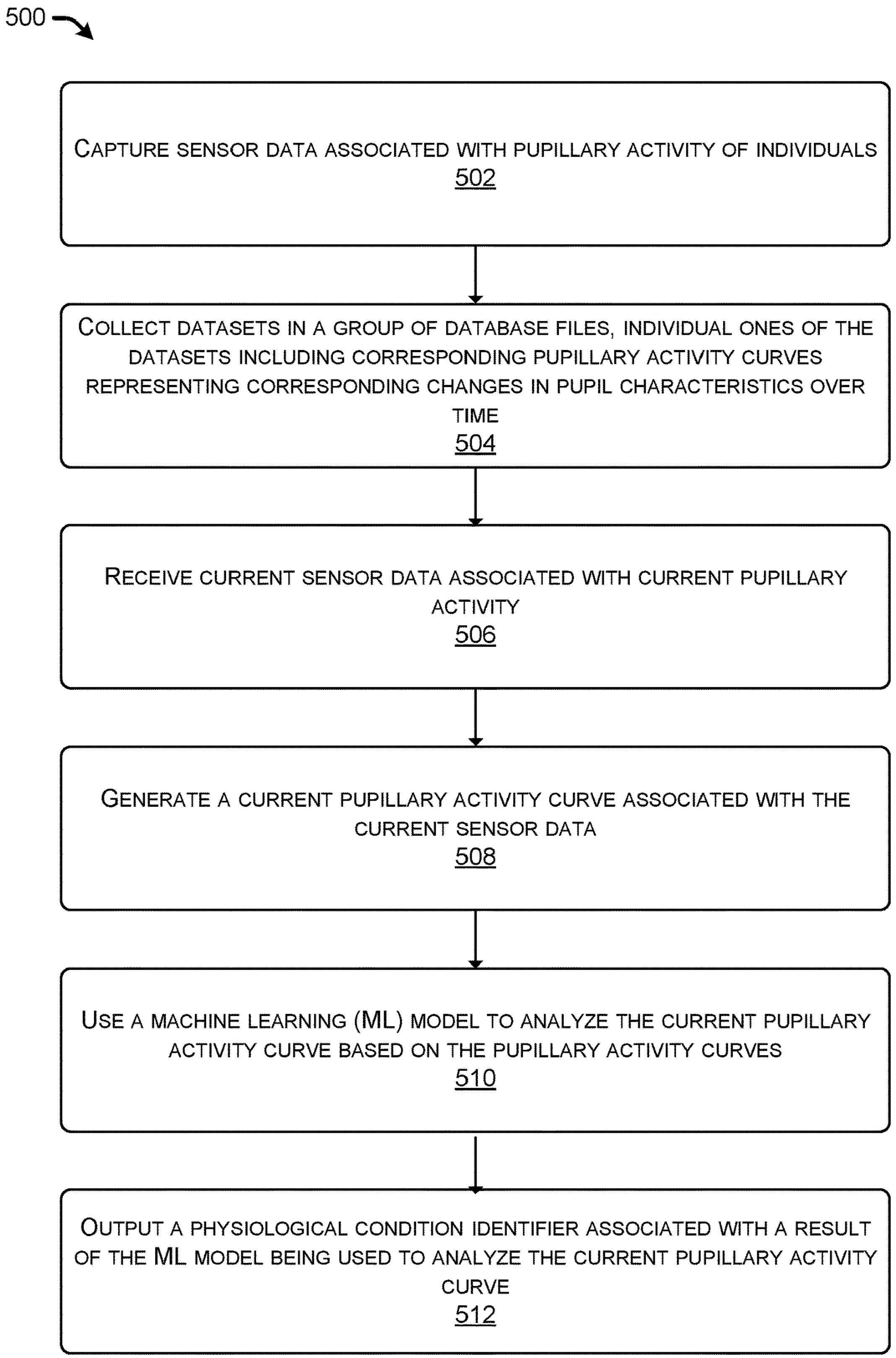
FIG. 5 depicts an example process for performing pupillary curve morphology and diagnosis management.

FIG. 5 depicts an example process 500 for performing pupillary curve morphology and diagnosis management.

At operation 502, the process can include capturing sensor data associated with pupillary activity of individuals. The sensor data (e.g., the sensor data 216) can be captured based on light emitted (e.g., output) by a computing device 114 and/or a camera 116. The sensor data 216 can be captured by the camera 116.

At operation 504, the process can include collecting datasets in a group of database files, individual ones of the datasets including corresponding pupillary activity curves representing corresponding changes in pupil characteristics over time. The datasets can include the pupillary data 218. Baselines can be generated via consolidation of pupillary activity data comprising the pupillary activity curves. The pupillary activity curves can include one or more pupillary curves (e.g., one or more pupil response curves) (e.g., one or more pupillary light reflex (PLR) curves) in the pupillary data 218.

At operation 506 the process can include receiving current sensor data associated with current pupillary activity. The current sensor data can be included in the sensor data 216.

At operation 508, the process can include generating a current pupillary activity curve associated with the current sensor data. The current pupillary activity curve can include a current pupil response curve in the pupillary data 218.

At operation 510, the process can include using a machine learning (ML) model to analyze the current pupillary activity curve based on the pupillary activity curves. The ML model can be one of the ML model(s) utilized by the ML model component(s) 112.

At operation 512, the process can include outputting a physiological condition identifier associated with a result of the ML model being used to analyze the current pupillary activity curve. The outputting (e.g., presenting, displaying, propagating, transmitting, etc.) of the physiological condition identifier can be performed, based on the pupil activity information 236, the classification information 238, and/or the physiological condition information 240, as one of the activity(ies) performed utilizing the action information 242.

The functions described herein may be implemented in hardware, software executed by a processor, firmware, or any combination thereof. If implemented in software executed by a processor, the functions may be stored on or transmitted over as one or more instructions or code on a computer-readable medium. Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, optical disk storage, removable/non-removable computer-readable media, volatile/non-volatile computer-readable medium, magnetic disk storage, or any other non-transitory medium that can be used to carry or store desired program code means in the form of instructions or data structures and that can be accessed by a general-purpose or special-purpose computer, or a general-purpose or special-purpose processor.

Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Combinations of the above are also included within the scope of computer-readable media.

Although various terms, including "user," "patient," "subject," and "operator" are used for simplicity and ease of explanation throughout the current disclosure, it is not limited as such. In some examples, any of the terms including "user," "patient," "subject," and "operator" and/or any other type of term associated with any person of any type, can be interpreted as being interchangeable and used in a similar way as any other term for purposes of implementing any of the techniques discussed herein.

Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations.

Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

From the foregoing it will be appreciated that, although specific examples have been described herein for purposes of illustration, various modifications may be made while remaining with the scope of the claimed technology. The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method comprising:

monitoring pupils of individuals in environments;

capturing, as received sensor data, sensor data associated with pupillary activity of the individuals;

collecting, as pupillary activity curves, individual ones of datasets in a group of database files comprising, as an array or a string of numbers, data of the received sensor data, individual ones of the pupillary activity curves representing a change in a pupil characteristic over time, the data being represented by a two-dimensional line;

generating classification models representing mathematically generated classifications of the pupillary activity curves based on physiological conditions associated with the pupillary activity curves, the mathematically generated classifications being identified via classification tags and being stored with the classification tags as a portion of library data in library databases, the library data comprising the pupillary activity curves, wherein generating the classification models comprises processing whole pupillary activity curves to identify patterns and characteristics for diagnosis of the physiological conditions without computing intermediate pupillary metrics prior to classification;

generating baselines via consolidation of pupillary activity data comprising the pupillary activity curves, individual ones of the baselines representing a known physiological curve without at least one of the physiological conditions, the baselines being identified via baseline tags and being stored with the baseline tags as another portion of the library data in the library databases;

training a machine learning (ML) model using the library data;

receiving current sensor data associated with current pupillary activity associated with a simultaneous scan of a pair of pupils of an individual in response to at least one of external or internal stimuli, wherein the simultaneous scan comprises binocular data collection for both pupils at a same time to identify how both pupils react to the at least one of external or internal stimuli;

generating a current pupillary activity curve associated with the current sensor data, the current pupillary activity curve representing changes of both pupils in the pair of pupils;

performing, by a curve classification algorithm and utilizing the ML model, a comparison between the current pupillary activity curve and the pupillary activity curves based on the baselines and the mathematically generated classifications; and outputting a physiological condition identifier associated with a result of the comparison.

2. The method of claim 1, wherein collecting the datasets further comprises calibrating the pupillary activity curves by:

collecting light level data associated with the environments in which the sensor data is captured;

collecting video data representing the pupillary activity;

transforming the video data into time series curve data associated with changes of diameters of the pupils over time; and collecting, as the pupillary activity curves which include pupillary light reflex (PLR) curves, the datasets based on the light level data, the video data, and the time series curve data.

3. The method of claim 1, wherein:

performing, by the ML model, the comparison between the current pupillary activity curve and the pupillary activity curves further comprises performing, via the ML model, support vector machine (SVM) analysis of the current pupillary activity curve based on the pupillary activity curves in the library databases; and outputting the physiological condition identifier further comprises outputting principal component analysis (PCA) data indicating a PCA condition with which the physiological condition identifier is associated.

4. The method of claim 1, further comprising:

maintaining the library data in the library databases by performing i) ongoing analysis of additional sensor data associated with additional individuals, ii) ongoing collection of additional pupillary activity curves based on the additional sensor data, iii) ongoing generation of additional classification models based on the additional pupillary activity curves, iv) updating of the baselines as updated baselines based on the additional pupillary activity curves, and v) updating of the library data based on the additional pupillary activity curves, the additional classification models, and the updated baselines, the additional classification models being utilized to relatively increase a level of accuracy of ongoing identification of additional physiological conditions associated with the additional pupillary activity curves.

5. The method of claim 1, wherein performing, by the ML model, the comparison between the current pupillary activity curve and the pupillary activity curves further comprises:

matching at least one characteristic of the individual with at least one corresponding characteristic of individual ones of a first subset of the individuals associated with the pupillary activity curves, the at least one characteristic comprising at least one of a gender, an age, or an eye color; and performing, by the ML model, the comparison between the current pupillary activity curve and a second subset of the pupillary activity curves associated with the first subset of the individuals.

6. The method of claim 1, wherein performing, by the ML model, the comparison between the current pupillary activity curve and the pupillary activity curves further comprises:

outputting, by the ML model, a predictive performance measurement associated with the current pupillary activity curve, the predictive performance measurement indicating a probability of a future likelihood of the individual experiencing at least one physiological condition, the at least one physiological condition comprising at least one of a coma or a vegetative state.

7. The method of claim 1, wherein performing, by the ML model, the comparison between the current pupillary activity curve and the pupillary activity curves further comprises:

analyzing, by the ML model, the current pupillary activity curve; and identifying, in response to the analyzing of the current pupillary activity curve, at least one physiological condition with which the physiological condition identifier is associated, the at least one physiological condition comprising at least one of an injury, intoxication, deception, a mental state, fatigue, dementia, toxins, a disease, a heart condition, or diabetes.

8. A system comprising:

one or more processors; and one or more non-transitory computer-readable media storing instructions that, when executed by the one or more processors, cause the system to perform operations comprising:

capturing sensor data associated with pupillary activity of individuals;

collecting datasets based on the sensor data, individual ones of the datasets including corresponding pupillary activity curves representing corresponding changes in pupil characteristics over time;

generating classification models representing classifications of the pupillary activity curves based on physiological conditions associated with the pupillary activity curves, wherein generating the classification models comprises processing whole pupillary activity curves to identify patterns and characteristics for diagnosis of the physiological conditions without computing intermediate pupillary metrics prior to classification;

generating baselines via consolidation of pupillary activity data comprising the pupillary activity curves;

receiving current sensor data associated with current pupillary activity associated with a simultaneous scan of a pair of pupils of an individual in response to at least one of external or internal stimuli, wherein the simultaneous scan comprises binocular data collection for both pupils at a same time to identify how both pupils react to the at least one of external or internal stimuli;

generating a current pupillary activity curve associated with the current sensor data, the current pupillary activity curve representing changes of both pupils in the pair of pupils;

using a machine learning (ML) model to analyze the current pupillary activity curve, the ML model having been trained based on the baselines and the classifications; and outputting a physiological condition identifier associated with a result of the ML model being used to analyze the current pupillary activity curve.

9. The system of claim 8, wherein individual ones of the pupillary activity curves are represented by corresponding two-dimensional lines.

10. The system of claim 8, wherein the classification models represent mathematically generated classifications based on the physiological conditions.

11. The system of claim 8, wherein individual ones of the classifications are identified via corresponding classification tags and stored with the classification tags as a portion of library data in library databases.

12. The system of claim 8, wherein individual ones of the baselines represent corresponding known physiological curves without at least one of the physiological conditions, the baselines are identified via baseline tags, and the baselines are stored with the baseline tags as a portion of library data in library databases.

13. The system of claim 8, wherein using the ML model to analyze the current pupillary activity curve further comprises performing a comparison utilizing a curve classification algorithm.

14. The system of claim 8, wherein collecting the datasets further comprises calibrating the pupillary activity curves by:

collecting light level data associated with environments in which the sensor data is captured;

collecting video data representing the pupillary activity;

transforming the video data into time series curve data associated with changes of characteristics of pupils of a user over time; and collecting, as the pupillary activity curves which include pupillary light reflex (PLR) curves, the datasets based on the light level data, the video data, and the time series curve data.

15. The system of claim 8, wherein collecting the datasets further comprises:

transforming video data into time series curve data associated with changes of diameters of pupils of the individuals over time; and collecting, as the pupillary activity curves which include pupillary light reflex (PLR) curves, the datasets based on the video data and the time series curve data.

16. One or more non transitory computer-readable media storing instructions executable by at least one processor, wherein the instructions, when executed by the at least one processor, cause the at least one processor to perform operations comprising:

capturing sensor data associated with pupillary activity of individuals;

collecting datasets in a group of database files, individual ones of the datasets including corresponding pupillary activity curves representing corresponding changes in pupil characteristics over time;

receiving current sensor data associated with current pupillary activity associated with a simultaneous scan of a pair of pupils of an individual in response to at least one of external or internal stimuli, wherein the simultaneous scan comprises binocular data collection for both pupils at a same time to identify how both pupils react to the at least one of external or internal stimuli;

generating a current pupillary activity curve associated with the current sensor data, the current pupillary activity curve representing changes of both pupils in the pair of pupils;

using one or more data algorithm models to analyze the current pupillary activity curve based on the pupillary activity curves; and outputting a physiological condition identifier associated with a result of the one or more data algorithm models being used to analyze the current pupillary activity curve.

17. The one or more non transitory computer-readable media of claim 16, wherein individual ones of the pupillary activity curves are represented by corresponding two-dimensional lines.

18. The one or more non transitory computer-readable media of claim 16, further comprising:

generating classification models representing mathematically generated classifications based on physiological conditions associated with the pupillary activity curves, wherein using the one or more data algorithm models to analyze the current pupillary activity curve further comprises performing a comparison based on the classifications.

19. The one or more non transitory computer-readable media of claim 16, further comprising:

generating classifications based on physiological conditions associated with the pupillary activity curves, wherein individual ones of the classifications are identified via corresponding classification tags and stored with the classification tags as a portion of library data in one or more curve library databases, and wherein using the one or more data algorithm models to analyze the current pupillary activity curve further comprises performing a comparison based on the classifications.

20. The method of claim 1, wherein the simultaneous scan comprises collecting the sensor data simultaneously and contemporaneously for both pupils in the pair of pupils, and wherein the current pupillary activity curve represents at least one change of both pupils in the pair of pupils, the at least one change comprising at least one of a change of diameter of both pupils in the pair of pupils or a change of size of both pupils in the pair of pupils.

* * * * *